United States Patent
Ilyinskii et al.

(10) Patent No.: US 9,066,978 B2
(45) Date of Patent: Jun. 30, 2015

(54) DOSE SELECTION OF ADJUVANTED SYNTHETIC NANOCARRIERS

(75) Inventors: Petr Ilyinskii, Cambridge, MA (US); Grayson B. Lipford, Watertown, MA (US); Charles Zepp, Hardwick, MA (US)

(73) Assignee: Selecta Biosciences, Inc., Watertown, MA (US)

(*) Notice: Subject to any disclaimer, the term of this patent is extended or adjusted under 35 U.S.C. 154(b) by 406 days.

(21) Appl. No.: 13/116,542

(22) Filed: May 26, 2011

(65) Prior Publication Data

US 2012/0027806 A1 Feb. 2, 2012

Related U.S. Application Data

(60) Provisional application No. 61/348,713, filed on May 26, 2010, provisional application No. 61/348,717, filed on May 26, 2010, provisional application No. 61/348,728, filed on May 26, 2010, provisional application No. 61/358,635, filed on Jun. 25, 2010.

(51) Int. Cl.

| | |
|---|---|
| A61K 9/00 | (2006.01) |
| A61K 45/00 | (2006.01) |
| A61K 47/06 | (2006.01) |
| A61K 39/00 | (2006.01) |
| A61K 39/38 | (2006.01) |
| A61K 45/06 | (2006.01) |
| A61K 9/51 | (2006.01) |

(Continued)

(52) U.S. Cl.
CPC ....... *A61K 45/06* (2013.01); *A61K 2039/55522* (2013.01); *A61K 9/5153* (2013.01); *A61K 31/4745* (2013.01); *A61K 31/7115* (2013.01); *A61K 33/06* (2013.01); *A61K 39/0013* (2013.01); *A61K 39/385* (2013.01); *A61K 39/39* (2013.01); *A61K 47/02* (2013.01); *A61K 47/22* (2013.01); *A61K 47/24* (2013.01); *A61K 47/48176* (2013.01); *A61K 47/482* (2013.01); *A61K 47/48215* (2013.01); *A61K 47/48853* (2013.01); *A61K 2039/555* (2013.01); *A61K 2039/55511* (2013.01); *A61K 2039/55555* (2013.01); *A61K 2039/6093* (2013.01)

(58) Field of Classification Search
CPC ......... A61K 9/00; A61K 45/00; A61K 47/48; A61K 39/38; A61K 2039/55; A61K 2039/55522

See application file for complete search history.

(56) References Cited

U.S. PATENT DOCUMENTS

| | | |
|---|---|---|
| 3,608,066 A | 9/1971 | Illartein |
| 3,996,355 A | 12/1976 | Lin et al. |

(Continued)

FOREIGN PATENT DOCUMENTS

| | | |
|---|---|---|
| CN | 1692943 A | 11/2005 |
| EP | 0 636 031 B1 | 9/1996 |

(Continued)

OTHER PUBLICATIONS

Diwan, 2004, Current Drug Delivery, vol. 1, pp. 405-412.*

(Continued)

*Primary Examiner* — Cherie M Stanfield
(74) *Attorney, Agent, or Firm* — Wolf, Greenfield & Sacks, P.C.

(57) ABSTRACT

Disclosed are synthetic nanocarrier compositions with coupled adjuvant compositions as well as related methods.

11 Claims, 9 Drawing Sheets

(51) Int. Cl.

| | | |
|---|---|---|
| *A61K 31/4745* | (2006.01) | |
| *A61K 31/7115* | (2006.01) | |
| *A61K 33/06* | (2006.01) | |
| *A61K 39/385* | (2006.01) | |
| *A61K 39/39* | (2006.01) | |
| *A61K 47/02* | (2006.01) | |
| *A61K 47/22* | (2006.01) | |
| *A61K 47/24* | (2006.01) | |
| *A61K 47/48* | (2006.01) | |

(56) References Cited

U.S. PATENT DOCUMENTS

| | | |
|---|---|---|
| 4,009,257 A | 2/1977 | Thomas et al. |
| 4,021,364 A | 5/1977 | Speiser et al. |
| 4,225,581 A | 9/1980 | Kreuter et al. |
| 4,631,211 A | 12/1986 | Houghten |
| 4,756,907 A | 7/1988 | Beck et al. |
| 4,929,624 A | 5/1990 | Gerster et al. |
| 4,950,432 A | 8/1990 | Mehta et al. |
| 4,994,281 A | 2/1991 | Muranishi et al. |
| 5,114,703 A | 5/1992 | Wolf et al. |
| 5,118,528 A | 6/1992 | Fessi et al. |
| 5,175,296 A | 12/1992 | Gerster |
| 5,213,812 A | 5/1993 | Ruiz |
| 5,229,490 A | 7/1993 | Tam |
| 5,389,640 A | 2/1995 | Gerster et al. |
| 5,395,937 A | 3/1995 | Nikolaides et al. |
| 5,500,161 A | 3/1996 | Andrianov et al. |
| 5,514,378 A | 5/1996 | Mikos et al. |
| 5,543,158 A | 8/1996 | Gref et al. |
| 5,565,215 A | 10/1996 | Gref et al. |
| 5,578,325 A | 11/1996 | Domb et al. |
| 5,582,172 A | 12/1996 | Papisov et al. |
| 5,605,899 A | 2/1997 | Gerster et al. |
| 5,620,708 A | 4/1997 | Amkraut et al. |
| 5,656,298 A | 8/1997 | Kitchell et al. |
| 5,663,153 A | 9/1997 | Hutcherson et al. |
| 5,733,572 A | 3/1998 | Unger et al. |
| 5,733,925 A | 3/1998 | Kunz et al. |
| 5,741,909 A | 4/1998 | Gerster et al. |
| 5,750,110 A | 5/1998 | Prieels et al. |
| 5,762,904 A | 6/1998 | Okada et al. |
| 5,792,475 A | 8/1998 | Davis et al. |
| 5,837,752 A | 11/1998 | Shastri et al. |
| 5,869,103 A | 2/1999 | Yeh et al. |
| 5,871,747 A | 2/1999 | Gengoux-Sedlik |
| 5,876,727 A | 3/1999 | Swain et al. |
| 5,898,031 A | 4/1999 | Crooke |
| 5,912,017 A | 6/1999 | Mathiowitz et al. |
| 5,916,539 A | 6/1999 | Pilgrimm |
| 5,916,597 A | 6/1999 | Lee et al. |
| 5,928,647 A | 7/1999 | Rock |
| 5,977,089 A | 11/1999 | Arimilli et al. |
| 5,977,366 A | 11/1999 | Gerster et al. |
| 5,985,325 A | 11/1999 | Nagi |
| 5,989,591 A | 11/1999 | Nagi |
| 6,005,087 A | 12/1999 | Cook et al. |
| 6,007,845 A | 12/1999 | Domb et al. |
| 6,031,086 A | 2/2000 | Switzer |
| 6,039,969 A | 3/2000 | Tomai et al. |
| 6,043,224 A | 3/2000 | Lee et al. |
| 6,060,082 A | 5/2000 | Chen et al. |
| 6,083,505 A | 7/2000 | Miller et al. |
| 6,107,094 A | 8/2000 | Crooke |
| 6,110,462 A | 8/2000 | Barbas et al. |
| 6,127,533 A | 10/2000 | Cook et al. |
| 6,130,082 A | 10/2000 | Majarian et al. |
| 6,132,723 A | 10/2000 | Malcolm |
| 6,159,502 A | 12/2000 | Russell-Jones et al. |
| 6,194,388 B1 | 2/2001 | Krieg et al. |
| 6,197,229 B1 | 3/2001 | Ando et al. |
| 6,207,646 B1 | 3/2001 | Krieg et al. |
| 6,218,371 B1 | 4/2001 | Krieg et al. |
| 6,225,460 B1 | 5/2001 | Bischofberger et al. |
| 6,232,082 B1 | 5/2001 | Ennifar et al. |
| 6,239,116 B1 | 5/2001 | Krieg et al. |
| 6,245,776 B1 | 6/2001 | Skwierczynski et al. |
| 6,254,890 B1 | 7/2001 | Hirosue et al. |
| 6,288,040 B1 | 9/2001 | Muller et al. |
| 6,306,640 B1 | 10/2001 | Nicolette |
| 6,309,669 B1 | 10/2001 | Setterstrom et al. |
| 6,329,381 B1 | 12/2001 | Kurimoto et al. |
| 6,348,462 B1 | 2/2002 | Gerster et al. |
| 6,365,187 B2 | 4/2002 | Mathiowitz et al. |
| 6,387,397 B1 | 5/2002 | Chen et al. |
| 6,399,754 B1 | 6/2002 | Cook |
| 6,403,779 B1 | 6/2002 | Kawasaki et al. |
| 6,444,192 B1 | 9/2002 | Mattrey |
| 6,465,654 B2 | 10/2002 | Gerster et al. |
| 6,486,168 B1 | 11/2002 | Skwierczynski et al. |
| 6,506,559 B1 | 1/2003 | Fire et al. |
| 6,544,518 B1 | 4/2003 | Friede et al. |
| 6,558,951 B1 | 5/2003 | Tomai et al. |
| 6,565,859 B1 | 5/2003 | Fricker et al. |
| 6,569,463 B2 | 5/2003 | Patel et al. |
| 6,585,980 B1 | 7/2003 | Chan et al. |
| 6,608,201 B2 | 8/2003 | Gerster et al. |
| 6,610,319 B2 | 8/2003 | Tomai et al. |
| 6,610,713 B2 | 8/2003 | Tracey |
| 6,632,671 B2 | 10/2003 | Unger |
| 6,635,283 B2 | 10/2003 | Edwards et al. |
| 6,656,469 B1 | 12/2003 | Svensson et al. |
| 6,686,472 B2 | 2/2004 | Gerster et al. |
| 6,693,086 B1 | 2/2004 | Dow et al. |
| 6,696,076 B2 | 2/2004 | Tomai et al. |
| 6,699,474 B1 | 3/2004 | Cerny |
| 6,723,429 B2 | 4/2004 | Bengs et al. |
| 6,747,156 B2 | 6/2004 | Johansson et al. |
| 6,767,702 B2 | 7/2004 | Mirkin et al. |
| 6,790,961 B2 | 9/2004 | Gerster et al. |
| 6,800,296 B1 | 10/2004 | Langer et al. |
| 6,800,624 B2 | 10/2004 | Crooks et al. |
| 6,811,975 B2 | 11/2004 | Cook et al. |
| 6,815,170 B1 | 11/2004 | Morton |
| 6,881,421 B1 | 4/2005 | Da Silveira et al. |
| 6,989,435 B2 | 1/2006 | Grainger et al. |
| 7,008,411 B1 | 3/2006 | Mandrusov et al. |
| 7,037,523 B2 | 5/2006 | Hussain et al. |
| 7,056,704 B2 | 6/2006 | Tuschl et al. |
| 7,078,196 B2 | 7/2006 | Tuschl et al. |
| 7,097,837 B2 | 8/2006 | Nielsen et al. |
| 7,129,222 B2 | 10/2006 | Van Nest et al. |
| 7,132,475 B2 | 11/2006 | Hubbell et al. |
| 7,147,862 B1 | 12/2006 | Prieels et al. |
| 7,149,574 B2 | 12/2006 | Yun et al. |
| 7,192,725 B2 | 3/2007 | Chan et al. |
| 7,223,398 B1 | 5/2007 | Tuck et al. |
| 7,238,711 B1 | 7/2007 | Grainger et al. |
| 7,247,502 B2 | 7/2007 | Ennifar et al. |
| 7,250,403 B2 | 7/2007 | Van Nest et al. |
| 7,250,499 B2 | 7/2007 | Mirkin et al. |
| 7,262,286 B2 | 8/2007 | Kandimalla et al. |
| 7,276,489 B2 | 10/2007 | Agrawal et al. |
| 7,285,289 B2 | 10/2007 | Nagy et al. |
| 7,357,936 B1 | 4/2008 | Garcon |
| 7,363,076 B2 | 4/2008 | Yun et al. |
| 7,375,180 B2 | 5/2008 | Gorden et al. |
| 7,387,271 B2 | 6/2008 | Noelle et al. |
| 7,390,780 B2 | 6/2008 | Huang et al. |
| 7,427,629 B2 | 9/2008 | Kedl et al. |
| 7,501,134 B2 | 3/2009 | O'Hagan et al. |
| 7,517,520 B2 | 4/2009 | Manolova et al. |
| 7,550,441 B2 | 6/2009 | Farokhzad et al. |
| 7,566,703 B2 | 7/2009 | Krieg et al. |
| 7,727,969 B2 | 6/2010 | Farokhzad et al. |
| 7,776,620 B2 | 8/2010 | Ennifar et al. |
| 7,842,312 B2 | 11/2010 | Burgermeister et al. |
| 8,367,113 B2 | 2/2013 | Gu et al. |
| 8,629,151 B2 | 1/2014 | Zepp et al. |
| 2002/0055477 A1 | 5/2002 | Nest et al. |
| 2002/0086356 A1 | 7/2002 | Tuschl et al. |
| 2002/0197269 A1 | 12/2002 | Lingnau et al. |
| 2003/0054042 A1 | 3/2003 | Liversidge et al. |

(56) References Cited

U.S. PATENT DOCUMENTS

| | | |
|---|---|---|
| 2003/0108565 A1 | 6/2003 | Johnson et al. |
| 2003/0108923 A1 | 6/2003 | Tuschl et al. |
| 2003/0133988 A1 | 7/2003 | Fearon et al. |
| 2003/0138432 A1 | 7/2003 | Glazier |
| 2003/0165478 A1 | 9/2003 | Sokoll |
| 2003/0175950 A1 | 9/2003 | McSwiggen |
| 2003/0223938 A1 | 12/2003 | Nagy et al. |
| 2003/0232013 A1 | 12/2003 | Sieckman et al. |
| 2004/0022840 A1 | 2/2004 | Nagy et al. |
| 2004/0038406 A1 | 2/2004 | Unger et al. |
| 2004/0059094 A1 | 3/2004 | Bachmann et al. |
| 2004/0067503 A1 | 4/2004 | Tan et al. |
| 2004/0092470 A1 | 5/2004 | Leonard et al. |
| 2004/0109894 A1 | 6/2004 | Shefer et al. |
| 2004/0141958 A1 | 7/2004 | Steinaa et al. |
| 2004/0142887 A1 | 7/2004 | Cui et al. |
| 2004/0156846 A1 | 8/2004 | Daum et al. |
| 2004/0191215 A1 | 9/2004 | Froix et al. |
| 2004/0192626 A1 | 9/2004 | McSwiggen et al. |
| 2004/0247680 A1 | 12/2004 | Farokhzad et al. |
| 2004/0258698 A1 | 12/2004 | Wightman et al. |
| 2005/0020525 A1 | 1/2005 | McSwiggen et al. |
| 2005/0032733 A1 | 2/2005 | McSwiggen et al. |
| 2005/0037075 A1 | 2/2005 | Farokhzad et al. |
| 2005/0042298 A1 | 2/2005 | Pardridge et al. |
| 2005/0048063 A1 | 3/2005 | Ruoslahti et al. |
| 2005/0074812 A1 | 4/2005 | Ruoslahti et al. |
| 2005/0107322 A1 | 5/2005 | O'Hagan et al. |
| 2005/0113697 A1 | 5/2005 | Ottoboni et al. |
| 2005/0158390 A1 | 7/2005 | Rana et al. |
| 2005/0163745 A1 | 7/2005 | Sokoll et al. |
| 2005/0191294 A1 | 9/2005 | Arap et al. |
| 2005/0192248 A1 | 9/2005 | Tsuji et al. |
| 2005/0239734 A1 | 10/2005 | Uhlmann et al. |
| 2005/0244504 A1 | 11/2005 | Little et al. |
| 2006/0002852 A1 | 1/2006 | Saltzman et al. |
| 2006/0002995 A1 | 1/2006 | Harwigsson |
| 2006/0051317 A1 | 3/2006 | Batrakova et al. |
| 2006/0073114 A1 | 4/2006 | Grainger et al. |
| 2006/0111271 A1 | 5/2006 | Cerny et al. |
| 2006/0142202 A1 | 6/2006 | Alkan et al. |
| 2006/0173339 A1 | 8/2006 | Tornes et al. |
| 2006/0189554 A1 | 8/2006 | Mumper et al. |
| 2006/0241076 A1 | 10/2006 | Uhlmann et al. |
| 2006/0251677 A1* | 11/2006 | Bachmann et al. ........ 424/204.1 |
| 2006/0257359 A1 | 11/2006 | Francois et al. |
| 2007/0014804 A1 | 1/2007 | Burkhard |
| 2007/0014807 A1 | 1/2007 | Maida, III |
| 2007/0087986 A1 | 4/2007 | Premack et al. |
| 2007/0098713 A1 | 5/2007 | Unger et al. |
| 2007/0116768 A1 | 5/2007 | Chorny et al. |
| 2007/0166384 A1 | 7/2007 | Zarraga et al. |
| 2007/0184068 A1 | 8/2007 | Renner et al. |
| 2007/0264481 A1 | 11/2007 | DeSimone et al. |
| 2007/0292386 A9 | 12/2007 | Campbell et al. |
| 2008/0014144 A1 | 1/2008 | Saltzman et al. |
| 2008/0014281 A1 | 1/2008 | Shibata et al. |
| 2008/0031899 A1 | 2/2008 | Reddy et al. |
| 2008/0044484 A1 | 2/2008 | Minev |
| 2008/0050450 A1 | 2/2008 | Arnold et al. |
| 2008/0081074 A1 | 4/2008 | Gu et al. |
| 2008/0145441 A1 | 6/2008 | Penades et al. |
| 2008/0160089 A1* | 7/2008 | Vitiello et al. ................ 424/489 |
| 2008/0171059 A1 | 7/2008 | Howland et al. |
| 2008/0207550 A1 | 8/2008 | Fearon et al. |
| 2008/0213377 A1 | 9/2008 | Bhatia et al. |
| 2008/0233181 A1 | 9/2008 | Nagy et al. |
| 2008/0234251 A1 | 9/2008 | Doherty et al. |
| 2008/0268063 A1 | 10/2008 | Jon et al. |
| 2008/0305161 A1 | 12/2008 | Shah et al. |
| 2008/0306050 A1 | 12/2008 | Doherty et al. |
| 2008/0317784 A1 | 12/2008 | O'Hagan et al. |
| 2009/0004118 A1 | 1/2009 | Nie et al. |
| 2009/0011009 A1 | 1/2009 | Benita et al. |
| 2009/0028910 A1 | 1/2009 | DeSimone et al. |
| 2009/0053293 A1 | 2/2009 | Liang et al. |
| 2009/0074828 A1 | 3/2009 | Alexis et al. |
| 2009/0104268 A1 | 4/2009 | Himmler et al. |
| 2009/0130210 A1 | 5/2009 | Raheja et al. |
| 2009/0155292 A1 | 6/2009 | Santamaria et al. |
| 2009/0169636 A1 | 7/2009 | O'Hagan et al. |
| 2009/0226525 A1 | 9/2009 | de los Rios et al. |
| 2009/0257950 A1 | 10/2009 | Sligar et al. |
| 2009/0297609 A1 | 12/2009 | Shoichet et al. |
| 2009/0297621 A1 | 12/2009 | Lim et al. |
| 2009/0298710 A1 | 12/2009 | Farokhzad et al. |
| 2009/0324551 A1 | 12/2009 | Carson et al. |
| 2009/0325292 A1 | 12/2009 | Baker et al. |
| 2010/0022680 A1 | 1/2010 | Karnik et al. |
| 2010/0055189 A1 | 3/2010 | Hubbell et al. |
| 2010/0062968 A1 | 3/2010 | Pulendran et al. |
| 2010/0068285 A1 | 3/2010 | Zale et al. |
| 2010/0069426 A1 | 3/2010 | Zale et al. |
| 2010/0092425 A1 | 4/2010 | Von Andrian et al. |
| 2010/0098770 A1 | 4/2010 | Ramalingam et al. |
| 2010/0104653 A1 | 4/2010 | Ludwig et al. |
| 2010/0111973 A1 | 5/2010 | Dranoff et al. |
| 2010/0129392 A1 | 5/2010 | Shi et al. |
| 2010/0129439 A1 | 5/2010 | Alexis et al. |
| 2010/0143453 A1 | 6/2010 | Schiffelers et al. |
| 2010/0144845 A1 | 6/2010 | Farokhzad et al. |
| 2010/0151000 A1 | 6/2010 | Thomas et al. |
| 2010/0160299 A1 | 6/2010 | Baker et al. |
| 2010/0166876 A1 | 7/2010 | Lewis et al. |
| 2010/0172993 A1 | 7/2010 | Singh et al. |
| 2010/0183727 A1 | 7/2010 | Iannacone et al. |
| 2010/0196482 A1 | 8/2010 | Radovic-Moreno et al. |
| 2010/0203142 A1 | 8/2010 | Zhang et al. |
| 2010/0233231 A1 | 9/2010 | Labrecque et al. |
| 2010/0233251 A1 | 9/2010 | Von Andrian et al. |
| 2010/0266491 A1 | 10/2010 | Farokhzad et al. |
| 2010/0297233 A1 | 11/2010 | Moretti et al. |
| 2010/0303723 A1 | 12/2010 | Farokhzad et al. |
| 2010/0303850 A1 | 12/2010 | Lipford et al. |
| 2010/0316724 A1 | 12/2010 | Whitfield et al. |
| 2010/0323019 A1 | 12/2010 | Lim et al. |
| 2010/0323199 A1 | 12/2010 | Gu et al. |
| 2011/0008435 A1 | 1/2011 | Devane et al. |
| 2011/0014281 A1 | 1/2011 | Aleksov et al. |
| 2011/0020388 A1 | 1/2011 | Zepp et al. |
| 2011/0027217 A1 | 2/2011 | Zepp et al. |
| 2011/0027368 A1 | 2/2011 | Burgermeister et al. |
| 2011/0052697 A1 | 3/2011 | Farokhzad et al. |
| 2011/0110965 A1 | 5/2011 | Fraser et al. |
| 2011/0151015 A1 | 6/2011 | Hubby et al. |
| 2011/0171248 A1 | 7/2011 | Pittet et al. |
| 2011/0223201 A1 | 9/2011 | Lipford et al. |
| 2011/0229556 A1 | 9/2011 | Irvine et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2011/0294717 A1 | 12/2011 | Ali et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0114677 A1 | 5/2012 | Zepp et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2013/0028857 A1 | 1/2013 | Gao et al. |

(56) References Cited

U.S. PATENT DOCUMENTS

| | | |
|---|---|---|
| 2013/0028941 A1 | 1/2013 | Altreuter et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado |
| 2013/0059009 A1 | 3/2013 | Kishimoto et al. |

FOREIGN PATENT DOCUMENTS

| | | |
|---|---|---|
| EP | 0 582 581 B1 | 5/1999 |
| EP | 1 221 955 B9 | 7/2002 |
| EP | 1 140 091 B1 | 9/2005 |
| EP | 1 752 141 A1 | 2/2007 |
| EP | 0 938 315 B1 | 7/2007 |
| WO | WO 92/15582 A1 | 9/1992 |
| WO | WO 95/22963 A1 | 8/1995 |
| WO | WO 96/20698 A2 | 7/1996 |
| WO | WO 97/04747 A1 | 2/1997 |
| WO | WO 97/47623 A1 | 12/1997 |
| WO | WO 98/08856 A2 | 3/1998 |
| WO | WO 98/37919 A1 | 9/1998 |
| WO | WO 98/40100 A1 | 9/1998 |
| WO | WO 98/52581 A1 | 11/1998 |
| WO | WO 99/56755 A1 | 11/1999 |
| WO | WO 00/06123 A1 | 2/2000 |
| WO | WO 00/27363 A1 | 5/2000 |
| WO | WO 00/44895 A1 | 8/2000 |
| WO | WO 00/50075 A2 | 8/2000 |
| WO | WO 01/68103 A2 | 9/2001 |
| WO | WO 01/75164 A2 | 10/2001 |
| WO | WO 02/32450 A2 | 4/2002 |
| WO | WO 02/100442 A2 | 12/2002 |
| WO | WO 03/086280 A2 | 10/2003 |
| WO | WO 2004/022594 A2 | 3/2004 |
| WO | WO 2004/030608 A2 | 4/2004 |
| WO | WO 2004/053104 A2 | 6/2004 |
| WO | WO 2004/058179 A2 | 7/2004 |
| WO | WO 2004/071493 A1 | 8/2004 |
| WO | WO 2004/084871 A1 | 10/2004 |
| WO | WO 2004/098509 A2 | 11/2004 |
| WO | WO 2005/014110 A1 | 2/2005 |
| WO | WO 2005/042018 A2 | 5/2005 |
| WO | WO 2005/058282 A1 | 6/2005 |
| WO | WO 2005/097993 A2 | 10/2005 |
| WO | WO 2005/110013 A2 | 11/2005 |
| WO | WO 2005/120574 A1 | 12/2005 |
| WO | WO 2006/031878 A2 | 3/2006 |
| WO | WO 2006/037979 A2 | 4/2006 |
| WO | WO 2006/066158 A2 | 6/2006 |
| WO | WO 2006/078278 A2 | 7/2006 |
| WO | WO 2006/117217 A2 | 11/2006 |
| WO | WO 2006/135434 A2 | 12/2006 |
| WO | WO 2007/001448 A2 | 1/2007 |
| WO | WO 2007/003054 A1 | 1/2007 |
| WO | WO 2007/019678 A1 | 2/2007 |
| WO | WO 2007/098254 A1 | 2/2007 |
| WO | WO 2007/040840 A2 | 4/2007 |
| WO | WO 2006/102395 A3 | 5/2007 |
| WO | WO 2007/062107 A2 | 5/2007 |
| WO | WO 2007/068747 A1 | 6/2007 |
| WO | WO 2007/070682 A2 | 6/2007 |
| WO | WO 2007/089870 A2 | 8/2007 |
| WO | WO 2007/109810 A2 | 9/2007 |
| WO | WO 2007/118653 A2 | 10/2007 |
| WO | WO 2007/133807 A2 | 11/2007 |
| WO | WO 2007/137117 A2 | 11/2007 |
| WO | WO 2007/144150 A1 | 12/2007 |
| WO | WO 2007/149802 A2 | 12/2007 |
| WO | WO 2007/150030 A2 | 12/2007 |
| WO | WO 2008/019142 A2 | 2/2008 |
| WO | WO 2008/033432 A2 | 3/2008 |
| WO | WO 2008/124639 A2 | 4/2008 |
| WO | WO 2008/051245 A2 | 5/2008 |
| WO | WO 2008/071774 A1 | 6/2008 |
| WO | WO 2008/079924 A1 | 7/2008 |
| WO | WO 2008/093173 A1 | 8/2008 |
| WO | WO 2008/105773 A2 | 9/2008 |
| WO | WO 2008/115319 A2 | 9/2008 |
| WO | WO 2008/115641 A2 | 9/2008 |
| WO | WO 2008/118861 A2 | 10/2008 |
| WO | WO 2008/121926 A1 | 10/2008 |
| WO | WO 2008/124632 A1 | 10/2008 |
| WO | WO 2008/124634 A1 | 10/2008 |
| WO | WO 2008/127532 A1 | 10/2008 |
| WO | WO 2008/129020 A1 | 10/2008 |
| WO | WO 2008/147456 A2 | 12/2008 |
| WO | WO 2006/137934 A3 | 3/2009 |
| WO | WO 2009/027971 A2 | 3/2009 |
| WO | WO 2009/051837 A2 | 4/2009 |
| WO | WO 2009051837 A2 * | 4/2009 |
| WO | WO 2009/076158 A1 | 6/2009 |
| WO | WO 2009/106999 A2 | 9/2009 |
| WO | WO 2009/109428 A2 | 9/2009 |
| WO | WO 2009/111588 A1 | 9/2009 |
| WO | WO 2009/158687 A1 | 12/2009 |
| WO | WO 2010/003009 A2 | 1/2010 |
| WO | WO 2010/017330 A1 | 2/2010 |
| WO | WO 2010/018130 A1 | 2/2010 |
| WO | WO 2010/018131 A1 | 2/2010 |
| WO | WO 2010/018132 A1 | 2/2010 |
| WO | WO 2010/018133 A1 | 2/2010 |
| WO | WO 2010/025324 A2 | 3/2010 |
| WO | WO 2010/037402 A1 | 4/2010 |
| WO | WO 2010/037566 A1 | 4/2010 |
| WO | WO 2010/042863 A1 | 4/2010 |
| WO | WO 2010/042866 A1 | 4/2010 |
| WO | WO 2010/042870 A1 | 4/2010 |
| WO | WO 2010/042876 A1 | 4/2010 |
| WO | WO 2010/123569 A2 | 10/2010 |
| WO | WO 2010/138192 A2 | 12/2010 |
| WO | WO 2010/138194 A2 | 12/2010 |
| WO | WO 2011/005850 A1 | 1/2011 |

OTHER PUBLICATIONS

Hatsukami, 2005, Clinical Pharmacology and Therapeutics, vol. 78, Issue 5, pp. 456-467.*
Diwan, 2002, Journal of Controlled Release, vol. 85, pp. 247-262.*
Malyala, 2008, Journal of Pharmaceutical Sciences, vol. 97, issue 3, pp. 1155-1165.*
Malyala, 2009, Advanced Drug Delivery Reviews, vol. 61, pp. 218-225.*
Maurer, 2005, European Journal of Immunology, vol. 35, pp. 2031-2040.*
Singh, 2004, Journal of Pharmaceutical Sciences, vol. 93, issue 2, pp. 273-282.*
Zolnik et al., (Endocrinology. Feb. 2010;151(2):458-465; published online Dec. 16, 2009).*
Ishida et al., (J Controlled Release. 2006;115:251-258; published online Sep. 3, 2006).*
[No Author Listed] Nanoparticles as Drug Carriers. Ed, Vladimir Torchilin. Imperial College Press. 2006. 754 pages.
[No Author Listed] R 848 Vanguard Medica phase change II, Europe. Highbeam Business. R & D Focus Drug News. Mar. 6, 2000. http://business.highbeam.com . . . Last Accessed Feb. 16, 2011. 1 page.
[No Author Listed] S-28463. Drugs Future. 1999;24(6):622-7.
Aime et al., Lanthanide(III) chelates for NMR biomedical applications. Chemical Society Reviews. 1998;27:19-29.
Akaishi et al., Targeting chemotherapy using antibody-combined liposome against human pancreatic cancer cell-line. The Tohoku Journal of Experimental Medicine. 1994;175(1):29-42.
Alexis et al., Factors affecting the clearance and biodistribution of polymeric nanoparticles. Mol Pharm. Jul.-Aug. 2008;5(4):505-15. Epub Aug. 4, 2008.

(56) References Cited

OTHER PUBLICATIONS

Allen et al., Nano-engineering block copolymer aggregates for drug delivery. Colloids Surfaces B-Biointerfaces. 1999;16:3-27.
Allison, The mode of action of immunological adjuvants. Dev Biol Stand. 1998;92:3-11.
Anderson et al., Delivery Systems for Immunomodulatory Proteins and Peptides. BioDrugs. Jan. 1997;7(1):51-65.
Anikeeva et al., Quantum dot/peptide-MHC biosensors reveal strong CD8-dependent cooperation between self and viral antigens that augment the T cell response. Proc Natl Acad Sci U S A. Nov. 7, 2006;103(45):16846-51. Epub Oct. 31, 2006.
Asano et al., Targeting activated lymphocytes with lipid microsphere containing a cytotoxic agent; efficacy of immunosuppression with a new drug delivery system. J Urology. 2001;165(5)384. Abstract 1571.
Astete et al., Synthesis and characterization of PLGA nanoparticles. J Biomat Sci. 2006;17:247-89.
Ataman-Onal et al., Surfactant-free anionic PLA nanoparticles coated with HIV-1 p24 protein induced enhanced cellular and humoral immune responses in various animal models. J Control Release. May 15, 2006;112(2):175-85. Epub Mar. 6, 2006.
Avgoustakis, Pegylated poly(lactide) and poly(lactide-co-glycolide) nanoparticles: preparation, properties and possible applications in drug delivery. Curr Drug Deliv. Oct. 2004;1(4):321-33.
Bachmann et al., T helper cell-independent neutralizing B cell response against vesicular stomatitis virus: role of antigen patterns in B cell induction?. Eur J Immunol. 1995;25(12):3445-51.
Badiee et al., Coencapsulation of CpG oligodeoxynucleotides with recombinant Leishmania major stress-inducible protein 1 in liposome enhances immune response and protection against leishmaniasis in immunized BALB/c mice. Clin Vaccine Immunol. Apr. 2008;15(4):668-74. Epub Jan. 30, 2008.
Bagalkot et al., An Aptamer-Doxorubicin Physical Conjugate as a Novel Targeted Drug-Delivery Platform. Angew Chem Int. 2006;45(48):8149-52.
Barchet et al., Virus-induced interferon alpha production by a dendritic cell subset in the absence of feedback si:nalin: in vivo. J Exp Med. 2002;195(4):507-16.
Bauer et al., Human TLR9 confers responsiveness to bacterial DNA via species-specific CpG motif recognition. Proc Natl Acad Sci U S A. Jul. 31, 2001;98(16):9237-42. Epub Jul. 24, 2001.
Beaurepaire et al., Functionalized Fluorescent Oxide Nanoparticles: Artificial Toxins for Sodium Channel Targeting and Imaging at the Single-Molecule Level. Nano Letters. 2004;4(11):2079-83.
Bei et al., "TAA polyepitope DNA-based vaccines: A potential tool for cancer therapy." J Biomed Biotech. 2010; 102758:1-12.
Blanco-Prieto et al., Slow delivery of the selective cholecystokinin agonist pBC 264 into the rat nucleus accumbens using microspheres. J Neurochem. Dec. 1996;67(6):2417-24.
Blander, Phagocytosis and antigen presentation: a partnership initiated by Toll-like receptors. Ann Rheum Dis. Dec. 2008;67 Suppl 3:iii44-9.
Bourquin et al., Targeting CpG oligonucleotides to the lymph node by nanoparticles elicits efficient antitumoral immunity. J Immunol. Sep. 1, 2008;181(5):2990-8.
Boussif et al., A versatile vector for gene and oligonucleotide transfer into cells in culture and in vivo: polyethylenimine. Proc Natl Acad Sci. USA. 1995;92:7297-301.
Brito et al., Nanoparticulate carriers for the treatment of coronary restenosis. Int J Nanomedicine. 2007;2(2):143-61.
Bullis, Shape Matters for Nanoparticles. Technology Review. Aug. 7, 2008. 2 pages.
Bundy et al., *Escherichia coli*-based cell-free synthesis of virus-like particles. Biotechnol Bioeng. May 1, 2008;100(1):28-37.
Burmeister et al., Direct in vitro selection of a 2'-0-methyl aptamer to VEGF. Chem Biol. 2005;12(1):25-33.
Carino et al., Nanos here based oral insulin delive . J Control Release. 2000;65(1-2):261-9.
Carrasco et al., B cells acquire particulate antigen in a macrophage-rich area at the boundary between the follicle and the subcapsular sinus of the lymph node.Immunity. Jul. 2007;27(1):160-71. Epub Jul. 19, 2007.
Casola et al., B cell receptor signal strength determines B cell fate. Nat Immunol. 2004;5(3):317-27.
Cerritelli et al., PEG-SS-PPS: reduction-sensitive disulfide block copolymer vesicles for intracellular drug delivery. Biomacromolecules. Jun. 2007;8(6):1966-72. Epub May 12, 2007.
Chacón et al., Optimized preparation of poly D,L (lactic-glycolic) microspheres and nanoparticles for oral administration. Intl J Pharmaceutics. 1996;141:81-91.
Chan et al.,Synthesis and immunological characterization of toll-like receptor 7 agonistic conjugates. Bioconjug Chem. Jun. 2009;20(6):1194-200.
Cheng et al., Formulation of functionalized PLGA-PEG nanoparticles for in vivo targeted drug delivery. Biomaterials. 2007;28(5):869-76.
Chinen et al., Basic and clinical immunology. J Allergy Clin Immunol. Aug. 2005;116(2):411-8.
Chu et al., Aptamer mediated siRNA delivery. Nuc Acid Res. 2006;34:e73.
Chu et al., CpG oligodeoxynucleotides act as adjuvants that switch on T helper 1 (Th1) immunity. J Exp Med. Nov. 17, 1997;186(10):1623-31.
Chu et al., Labeling tumor cells with fluorescent nanocrystal-aptamer bioconjugates. Biosens Bioelectron. 2006;21:1859-66.
Chukwu et al., Loading some psychopharmacologic agents onto poly(butylcynoacrylate) nanoparticles—a means for targeting agents to the brain and improving therapeutic efficiency. Proc Int'l Symp control Ret Bioact Mat 1999. 1148-9.
Clark, The reticulum of lymph nodes in mice studied with the electron microscope. Am J Anat. 1962;110:217-57.
Connor et al., Ex vivo evaluation of anti-EpCAM immunocytokine huKS-1L2 in ovarian cancer. J Immunother. 2004;27(3):211-19.
Conti et al., Thymopentin loaded microsphere preparation by w/o/w emulsion technique: in vitro/ex vivo evaluation. J Microencapsul. May-Jun. 1997;14(3):303-10.
Croy et al., Polymeric micelles for drug delivery. Curr Pharm Design. 2006;12:4669-84.
Cruz et al., The influence of PEG chain length and targeting moiety on antibody-mediated delivery of nanoparticle vaccines to human dendritic cells. Biomaterials. Oct. 2011;32(28):6791-803. Epub Jul. 2, 2011. E-pub version.
Dang et al., Stimulation of B lymphocytes through surface Ig receptors induces LFA-1 and ICAM-1-dependent adhesion. J Immunol. 1991;146(10):3273-9.
Davis et al., CpG DNA is a potent enhancer of specific immunity in mice immunized with recombinant hepatitis B surface antigen. J Immunol. Jan. 15, 1998;160(2):870-6.
De Gregorio et al., Alum adjuvanticity: unraveling a century old mystery. Eur J Immunol. Aug. 2008;38(8):2068-71.
De Jaeghere et al., Freeze-drying and lyopreservation of diblock and triblock poly(lactic acid)-poly(ethylene oxide) (PLA-PEO) copolymer nanoparticles. Pharm Dev Technol. 2000;5(4):473-83.
De La Fuente et al., Novel hyaluronan-based nanocarriers for transmucosal delivery of macromolecules. Macromol Biosci. May 13, 2008;8(5):441-50.
Delemarre et al., Repopulation of macrophages in popliteal lymph nodes of mice after liposome-mediated depletion. J Leukoc Biol. 1990;47(3):251-7.
Demangel et al., Single chain antibody fragments for the selective targeting of antigens to dendritic cells. Mol Immunol. May 2005;42(8):979-85. Epub Dec. 10, 2004.
Demello et al., Microscale reactors: nanoscale products. Lab on a Chip. 2004;4(2):11N-15N.
Demello, Control and detection of chemical reactions in microfluidic systems. Nature. 2006;442(7101):394-402.
Deming, Facile synthesis of block copolypeptides of defined architecture. Nature. 1997;390(6658):386-9.
Derfus et al., Intracellular Delivery of Quantum Dots for Live Cell Labeling and Organelle Tracking. Adv Mat. 2004;16:961-6.

(56) References Cited

OTHER PUBLICATIONS

Diethelm-Okita et al., Universal epitopes for human CD4+ cells on tetanus and diphtheria toxins. J Infect Dis. Mar. 2000;181(3):1001-9.
DiLillo et al., B10 cells and regulatory B cells balance immune responses during inflammation, autoimmunity, and cancer. Ann N Y Acad Sci. Jan. 2010;1183:38-57.
Diwan et al., Enhancement of immune responses by co-delivery of a CpG oligodeoxynucleotide and tetanus toxoid in biodegradable nanospheres. J Control Release. Dec. 2002 13;85(1-3):247-62.
Dockrell et al., Imiquimod and resiquimod as novel immunomodulators. J Antimicrob Chemother. Dec. 2001;48(6):751-5.
Dou et al., Development of a macrophage-based nanoparticle platform for antiretroviral drug delivery. Blood. Oct. 15, 2006;108(8):2827-35. Epub Jun. 29, 2006. Erratum in: Blood. Mar. 1, 2007;109(5):1816.
Donbrow, Ed., Microcapsules and Nanoparticles in Medicine and Pharmacy. CRC Press, Boca Raton, 1992.
Dykxhoorn et al., Killing the messenger: short RNAs that silence gene expression. Nat Rev Mol Cell Biol. 2003;4(6):457-67.
Elamanchili et al., "Pathogen-mimicking" nanoparticles for vaccine delivery to dendritic cells. J Immunother. May-Jun. 2007;30(4):378-95. Abstract only.
Elbashir et al., RNA interference is mediated by 21- and 22-nucleotide RNAs. Genes Dev. 2001;15(2):188-200.
Eldridge et al., Biodegradable microspheres as a vaccine delivery system. Mol Immunol. 1991;28(3):287-94.
Farokhzad et al., Impact of nanotechnology on drug delivery. ACS Nano. Jan. 27, 2009;3(1):16-20.
Farokhzad et al., Nanoparticle—aptamer bioconjugates for cancer targeting. Expert Opin Drug Deliv. 2006;3(3):311-24.
Farokhzad et al., Nanoparticle-Aptamer Bioconjugates: A New Approach for Targeting Prostate Cancer Cells. Cancer Research. 2004;64:7668-72.
Farokhzad et al., Targeted nanoparticle-aptamer bioconjugates for cancer chemotherapy in vivo. Proc Natl Acad Sci USA. 2006;103(16):6315-20.
Farr et al., The structure of the sinus wall of the lymph node relative to its endocytic properties and transmural cell passage. Am J Anat. 1980;157(3):265-84.
Feuillet et al., Involvement of Toll-like receptor 5 in the recognition of flagellated bacteria. Proc Natl Acad Sci U S A. Aug. 15, 2006;103(33):12487-92. Epub Aug. 4, 2006.
Fire et al., Potent and specific genetic interference by double-stranded RNA in *Caenorhabditis elegans*. Nature. 1998;391(6669):806-11.
Fonseca et al., Paclitaxel-loaded PLGA nanoparticles: preparation, physicochemical characterization and in vitro anti-tumoral activity. J Control Release. 2002;83(2):273-86.
Forslund et al., Nitric oxide-releasing particles inhibit phagocytosis in human neutrophils. Biochem Biophys Res Commun. Apr. 17, 1997;233(2):492-5.
Frederick et al., Structural comparison of anticancer drug-DNA complexes: adriamycin and daunomycin. Biochemistry. 1990;29(10):2538-49.
Gao et al., In vivo cancer targeting and imaging with semiconductor quantum dots. Nat Biotechnol. 2004;22(8):969-76.
Gao et al., In vivo molecular and cellular imaging with quantum dots. Curr Op Biotechnol. 2005;16:63-72.
Garçon et al., Boosting vaccine power. Sci Am. Oct. 2009;301(4):72-9.
Gelperina et al., The potential advantages of nanoparticle drug delivery systems in chemotherapy of tuberculosis. Am J Respir Crit Care Med. Dec. 15, 2005;172(12):1487-90. Epub Sep. 8, 2005.
Gref et al., Biodegradable long-circulating polymeric nanospheres. Science. 1994;263(5153):1600-3.
Griset et al., Expansile nanoparticles: synthesis, characterization, and in vivo efficacy of an acid-responsive polymeric drug delivery system. J Am Chem Soc. Feb. 25, 2009;131(7):2469-71. Epub Jan. 30, 2009.

Griset, Dissertation entitled: Delivery of Paclitaxel via pH-Responsive Polymeric Nanoparticles for Prevention of Lung Cancer and Mesothelioma Recurrence, Ohio State University, 2003.
Gu et al., Precise engineering of targeted nanoparticles by using self-assembled biointegrated block copolymers. Proc Natl Acad Sci U S A. Feb. 19, 2008;105(7):2586-91. Epub Feb. 13, 2008.
Haas et al., Sequence independent interferon-alpha induction by multimerized phosphodiester DNA depends on spatial regulation of Toll-like receptor-9 activation in plasmacytoid dendritic cells. Immunology. Feb. 2009;126(2):290-8. Epub Nov. 15, 2008.
Haensler et al., Polyamidoamine cascade polymers mediate efficient transfection of cells in culture. Bioconjugate Chem. 1993;4(5):372-9.
Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. Epub Aug. 3, 2008.
Hamdy et al., Pharmaceutical analysis of synthetic lipid A-based vaccine adjuvants in poly (D,L-lactic-co-glycolic acid) nanoparticle formulations. J Pharm Biomed Anal. Aug. 15, 2007;44(4):914-23. Epub Mar. 19, 2007.
Hammerbeck et al., Administration of a dual toll-like receptor 7 and toll-like receptor 8 agonist protects against influenza in rats. Antiviral Res. Jan. 2007;73(1):1-11. Epub Aug. 18, 2006.
Hanes et al., Polymer microspheres for vaccine delivery. Pharm Biotechnol. 1995;6:389-412.
Hangartner et al., Antiviral immune responses in gene-targeted mice expressing the immunoglobulin heavy chain of virus-neutralizing antibodies. Proc Natl Acad Sci USA. 2003;100:12883-88.
Hannon et al., Unlocking the potential of the human genome with RNA interference. Nature. 2004;431(7006):371-8.
Harada et al., Supramolecular assemblies of block copolymers in aqueous media as nanocontainers relevant to biological applications. Progress Polymer Sci. 2006;31(11):949-82.
Harper et al., Efficacy of a bivalent Li virus-like particle vaccine in prevention of infection with human papillomavirus types 16 and 18 in young women: a randomised controlled trial. Lancet., 2004;364(9447):1757-65.
Haseloff et al., Simple RNA enzymes with new and highly specific endoribonuclease activities. Nature. 1988;334(6183):585-91.
Hattermann et al., The Toll-like receptor 7/8-ligand resiquimod (R-848) primes human neutrophils for leukotriene B4, prostaglandin E2 and platelet-activating factor biosynthesis. FASEB J. May 2007;21(7):1575-85. Epub Jan. 30, 2007.
Hawiger et al., Dendritic cells induce peripheral T cell unresponsiveness under steady state conditions in vivo. J Exp Med. 2001;194(6):769-79.
Heeg et al., Structural requirements for uptake and recognition of CpG oligonucleotides. Int J Med Microbiol. Jan. 2008;298(1-2):33-8. Epub Aug. 13, 2007.
Heil et al., Species-specific recognition of single-stranded RNA via toll-like receptor 7 and 8. Science, Mar. 5, 2004;303(5663): 1526-9. Epub Feb. 19, 2004.
Hemmi et al., A Toll-like receptor recognizes bacterial DNA. Nature. Dec. 7, 2000;408(6813):740-5.
Hood et al., Tumor regression by targeted gene delivery to the neovasculature. Science. Jun. 28, 2002;296(5577):2404-7.
Hruby et al., Poly (ethylene oxide)-coated polymide nanoparticles deradable by glutathione. Colloid Polym Sci. 2007;285:569-74.
Johnson et al., Mechanism for rapid self-assembly of block copolymer nanoparticles. Phys Rev Lett. 2003;91(11):118302.1-4.
Jones et al., Polymeric micelles—a new generation of colloidal drug carriers. Eur J Pharmaceutics Biopharmaceutics. 1999;48:101-11.
Jordan et al., Promotion of B cell immune responses via an alum-induced myeloid cell population. Science. Jun. 18, 2004;304(5678):1808-10.
Jung et al., Tetanus Toxoid Loaded Nanoparticles from Sulfobutylated Poly(Vinyl Alcohol)-GraftPoly(Lactide-co-Glycolide): Evaluation of Antibody Response After Oral and Nasal Application in Mice. Pharm Res. 2001;18(3):352-60.
Junt et al., Subcapsular sinus macrophages in lymph nodes clear lymph-borne viruses and present them to antiviral B cells. Nature. 2007;450:110-4. Supplemental material.

(56) References Cited

OTHER PUBLICATIONS

Jurk et al., Human TLR7 or TLR8 independently confer responsiveness to the antiviral compound R-848. Nat Immunol. Jun. 2002;3(6):499.
Kabanov et al., DNA Complexes with Polycations for the Delivery of Genetic Material into Cells. Bioconjugate Chem. 1995;6(1):7-20.
Kamentsky, Laser scanning cytometry. Methods Cell Biol. 2001;63:51-87.
Kanchan et al., Interactions of antigen-loaded polylactide particles with macrophages and their correlation with the immune response. Biomaterials. Dec. 2007;28(35):5344-57. Epub Sep. 7, 2007.
Karrer et al., on the key role of secondary lymphoid organs in antiviral immune responses studied in alymphoplastic (aly/aly) and spleenless (Hox11(−)/−) mutant mice. J Exp Med. 1997;185(12):2157-70.
Kelly et al., The Optical Properties of Metal Nanoparticles: The Influence of Size, Shape, and Dielectric Environment. J Phys Chem B. 2003;107(3):668-77.
Kimura et al., Binding of oligoguanylate to scavenger receptors is required for oligonucleotides to augment NK cell activity and induce IFN. J Biochem. Nov. 1994;116(5):991-4.
Konan et al., Preparation and characterization of sterile sub-200 nm meso-tetra(4-hydroxylphenyl)porphyrin-loaded nanoparticles for photodynamic therapy. Eur J Pharm Biopharm. Jan. 2003;55(1):115-24.
Krieg et al., CpG motifs in bacterial DNA trigger direct B-cell activation. Nature. 1995;374(6522):546-9.
Kukowska-Latallo et al., Efficient transfer of genetic material into mammalian cells using Starburst polyamidoarnine dendrimers. Proc Natl Acad Sci USA. 1996;93(10):4897-902.
Labhasetwar et al., Arterial uptake of biodegradable nanoparticles: Effect of surface modifications. J Pharm Sci. 1998;87(10):1229-34.
Langer, Biomaterials in drug delivery and tissue engineering: one laboratory's experience. Acc Chem Res. 2000;33(2):94-101.
Langer, New methods of drug delivery. Science. 1990;249(4976):1527-33.
Langer, Selected advances in drug delivery and tissue engineering. J Control Release. 1999;62:7-11.
Leopold et al., Fluorescent virions: dynamic tracking of the pathway of adenoviral gene transfer vectors in living cells. Hum Gene Ther. 1998;9(3):367-78.
Leucuta et al., Albumin microspheres as a drug delivery system for epirubicin: pharmaceutical, pharmacokinetic and biological aspects. Int J Phar. 1988;41:213-7.
Liang et al., Activation of human B cells by phosphorothioate oligodeoxynucleotides. J Clin Invest. Sep. 1, 1996;98(5):1119-29.
Liang et al., Paclitaxel-Loaded Poly(γ-glutamic acid)-poly(lactide) Nanoparticles as a Targeted Drug Delivery System against Cultured HepG2 Cells. Bioconjug Chem. Mar.-Apr. 2006;17(2):291-9. E-pub ahead of print. E-pub version.
Lim et al., A Self-Destroying Polycationic Polymer: Biodegradable Poly(4-hydroxy-lproline ester). J Am Chem Soc. 1999;121(24):5633-9.
Lim et al., Cationic hyperbranched poly(amino ester): a novel class of DNA condensing molecule with cationic surface, biodegradable three-dimensional structure, and tertiary amine groups in the interior. J Am Chem Soc. Mar. 14, 2001;123(10):2460-1.
Lin et al., Well-Ordered Mesoporous Silica Nanoparticles as Cell Markers. Chem Mater. 2005;17:4570-3.
Lipford et al., Bacterial DNA as immune cell activator. Trends Microbiol. Dec. 1998;6(12):496-500.
Lipford et al., CpG-containing synthetic oligonucleotides promote B and cytotoxic T cell responses to protein antigen: a new class of vaccine adjuvants. Eur J Immunol. Sep. 1997;27(9):2340-4.
Lloyd, Disulphide reduction in lysosomes. The role of cysteine. Biochem J. Jul. 1, 1986;237(1):271-2.
Lönnberg, Solid-phase synthesis of oligonucleotide conjugates useful for delivery and targeting of potential nucleic acid therapeutics. Bioconjug Chem. Jun. 2009;20(6):1065-94.
Low et al., Folate receptor-targeted drugs for cancer and inflammatory diseases. Adv Drug Deliv Rev. 2004;56(8):1055-8.

Ludewig et al., Induction of optimal anti-viral neutralizing B cell responses by dendritic cells requires transport and release of virus particles in secondary lymphoid organs. Eur J Immunol. 2000;30(1):185-96.
Lupold et al., Identification and characterization of nuclease-stabilized RNA molecules that bind human prostate cancer cells via the prostate-specific membrane antigen. Cancer Res. 2002;62(14):4029-33.
Malyala et al., Enhancing the therapeutic efficacy of CpG oligonucleotides using biodegradable microparticles. Adv Drug Deliv Rev. Mar. 28, 2009;61(3):218-25. Epub Jan. 11, 2009.
Malyala et al., The potency of the adjuvant, CpG oligos, is enhanced by encapsulation in PLG microparticles. J Pharm Sci. Mar. 2008;97(3):1155-64.
Manolova et al., Nanoparticles target distinct dendritic cell populations according to their size. Eur J Immunol. 2008;38:1404-13.
Martinez-Pomares et al., Antigen presentation the macrophage way. Cell. Nov. 16, 2007;131(4):641-3.
Mathiowitz et al., Novel microcapsules for delivery systems. Reactive Polymers. 1987;6:275-83.
Mathiowitz et al., Polyanhydride Microspheres as Drug Carriers I. Hot Melt Encapsulation. J Control Release. 1987;5:13-22.
Mathiowitz et al., Polyanhydride Microspheres as Drug Carriers II.. Microencapsulation by Solvent Removal. J Appl Polymer Sci. 1988;35:755-74.
Mattheakis et al., Optical coding of mammalian cells using semiconductor quantum dots. Anal Biochem. 2004;327(2):200-8.
Maye et al., Comparison of the phagocytosis of two types of cyclosporin (SDZ OXL 400 and SDZ IMM 125) by alveolar macrophages from hamsters. Cell Biol Toxicol. Dec. 1998;14(6):411-8.
McSorley et al., Bacterial flagellin is an effective adjuvant for CD4+ T cells in vivo. J Immunol. Oct. 1, 2002;169(7):3914-9.
Meister et al., Mechanisms of gene silencing by double-stranded RNA. Nature. 2004;431(7006):343-9.
Mempel et al., T-cell priming by dendritic cells in lymph nodes occurs in three distinct phases. Nature. 2004;427(6970):154-9.
Metelitsa et al., Antidisialoganglioside/granulocyte macrophage-colonystimulating factor fusion protein facilitates neutrophil antibody-dependent cellular cytotoxicity and depends on FcγRII (CD32) and Mac-1 (CD11b/CD18) for enhanced effector cell adhesion and azurophil granule exocytosis. Blood. 2002;99(11):4166-73.
Michiels et al., Patent exemption for clinical trials: current status of the Bolar-type provisions in Europe. Life Sciences Intellectual Property Review 2008. Lavoix. www.worldipreview.com. 2008:68-70.
Milligan et al., Synthesis of small RNAs using T7 RNA polymerase. Methods Enzymol. 1989;180:51-62.
Moghimi et al., Long-circulating and target-specific nanoparticles: theory to practice. Pharmacol Rev. 2001;53(2):283-318.
Moghimi et al., Nanomedicine: current status and future prospects. FASEB J. Mar. 2005;19(3):311-30.
Mulligan, The basic science of gene therapy. Science. 1993;260(5110):926-32.
Murray et al., Synthesis and characterization of monodisperse nanocrystals and close-packed nanocrystal assemblies. Ann Rev Mat Sci. 2000;30:545-610.
Nakase et al., Biodegradable microspheres targeting mucosal immune-regulating cells: new approach for treatment of inflammatory bowel disease. J Gastroenterol. Mar. 2003;38 Suppl 15:59-62.
Nielson et al., Therapeutic efficacy of anti-ErbB2 immunoliposomes targeted by a phage antibody selected for cellular endocytosis. Biochim Biophys Acta. Aug. 19, 2002;1591(1-3):109-118.
Nikou et al., A HER-2/neu peptide admixed with PLA microspheres induces a Th1-biased immune response in mice. Biochim Biophys Acta. Sep. 15, 2005;1725(2):182-9.
Ochsenbein et al., Control of early viral and bacterial distribution and disease by natural antibodies. Science. 1999;286(5447):2156-9.
Ochsenbein et al., Protective T cell-independent antiviral antibody responses are dependent on complement. J Exp Med. 1999;190(8):1165-74.
Okada et al., Antigen-engaged B cells undergo chemotaxis toward the T zone and form motile conjugates with helper T cells. PLoS Biol. 2005;3(6):e150. 1047-61.

(56) References Cited

OTHER PUBLICATIONS

Olivier et al., Synthesis of pegylated immunonanoparticles. Pharm Res. Aug. 2002;19(8):1137-43.
Ong et al., Redox-triggered contents release from liposomes. J Am Chem Soc. Nov. 5, 2008;130(44):14739-44. Epub Oct. 8, 2008.
Pape et al., The humoral immune response is initiated in lymph nodes by B cells that acquire soluble antigen directly in the follicles. Immunity. 2007;26(4):491-502.
Pasqualini et al., Aminopeptidase N is a receptor for tumor-homing peptides and a target for inhibiting angiogenesis. Cancer Res. 2000;60(3):722-7.
Patri et al., Synthesis and in Vitro Testing of J591 Antibody—Dendrimer Conjugates for Targeted Prostate Cancer Therapy. Bioconj Chem. 2004;15:1174-81.
Pellegrino et al., On the development of colloidal nanoparticles towards multifunctional structures and their possible use for biological applications. Small. 2005;1(1):48-63.
Phillips et al., Enhanced antibody response to liposome-associated protein antigens: preferential stimulation of IgG2a/b production. Vaccine. 1992;10(3):151-8.
Pimentel et al., Peptide nanoparticles as novel immunogens: design and analysis of a prototypic severe acute respiratory syndrome vaccine. Chem Biol Drug Des. Jan. 2009;73(1):53-61.
Pockros, Current Status of Immunomodulatory Therapies in HCV Infection. Current Hepatitis Reports. 2004;3:16-22.
Popielarski et al., A nanoparticle-based model delivery system to guide the rational design of gene delivery to the liver. 2. In vitro and in vivo uptake results. Bioconjug Chem. Sep.-Oct. 2005;16(5):1071-80.
Purcell et al., Dissecting the role of peptides in the immune response: theory, practice and the application to vaccine design. J Pept Sci. May 2003;9(5):255-81.
Purcell et al., More than one reason to rethink the use of peptides in vaccine design. Nat Rev Drug Discov. May 2007;6(5):404-14.
Qi et al., Extrafollicular activation of lymph node B cells by antigen-bearing dendritic cells. Science. 2006;312(5780):1672-6.
Qiu et al., PLA-coated gold nanoparticles for the labeling of PLA biocarriers. Chem Mater. 2004;16:850-6.
Quintanar-Guerrero et al., Preparation Techniques and Mechanisms of Formation of Biodegradable Nanoparticles from Preformed Polymers. Drug Dev Industrial Pharmacy. 1998;24(12):1113-28.
Raman et al., Peptide Based Nanoparticles as a Platform for Vaccine Design. http://www.nsti.org/Nanotech2005/showabstract.html?absno=637. 2005. Abstract Only.
Reddy et al., Exploiting lymphatic transport and complement activation in nanoparticle vaccines. Nat Biotech. 2007;25(10):1159-64.
Reif et al., Balanced responsiveness to chemoattractants from adjacent zones determines B-cell position. Nature. 2002;416(6876):94-9.
Reis et al., Nanoencapsulation I. Methods for preparation of drug-loaded polymeric nanoparticles. Nanomedicine. 2006;2:8-21.
Richardson, The Synthesis and Chemistry of Certain 2-Substituted 5,6-Dihydroimidazo-, -oxazolo-, and -thiazolo[ij]quinolines. 1963;28:2581-7.
Robbins et al., Stable expression of shRNAs in human CD34+ progenitor cells can avoid induction of interferon responses to siRNAs in vitro. Nature Biotechnology. 2006;24(5):566-71.
Roman et al., Immunostimulatory DNA sequences function as T helper-1-promoting adjuvants. Nat Med. Aug. 1997;3(8):849-54.
Rossbacher et al, The B cell receptor itself can activate complement to provide the complement receptor 1/2 ligand required to enhance B cell immune responses in vivo. J Exp Med. 2003;198(4):591-602.
Salio et al., Modulation of human natural killer T cell ligands on TLR-mediated antigen-presenting cell activation. Proc Natl Acad Sci U S A. Dec. 18, 2007;104(51):20490-5. Epub Dec. 11, 2007.
Salmeron et al., Encapsulation Study of 6-Methylprednisolone in Lipid Microspheres. Drug Develop Indust Pharm. 1997;23(2):133-6.
Schultz et al., Single-target molecule detection with nonbleaching multicolor optical immunolabels. Proc Natl Acad Sci USA. 2000;97(3):996-1001.
Schultz, Plasmon resonant particles for biological detection. Curr Op Biotechnol. 2003;14:13-22.
Shahiwala et al., Nanocarriers for systemic and mucosal vaccine delivery. Recent Pat Drug Deliv Formul. 2007;1(1):1-9.
Sharma et al., Pharmaceutical aspects of intranasal delivery of vaccines using particulate systems. J Pharm Sci. Mar. 2009;98(3):812-43.
Shen et al., Enhanced and prolonged cross-presentation following endosomal escape of exogenous antigens encapsulated in biodegradable nanoparticles. Immunol. 2006;117:78-88.
Shestopalov et al., Multi-step synthesis of nanoparticles performed on millisecond time scale in a microfluidic droplet-based system. Lab Chip. 2004;4(4):316-21.
Shiow et al., CD69 acts downstream of interferon-alpha/beta to inhibit S1P1 and lymphocyte egress from lymphoid organs. Nature. Mar. 23, 2006;440(7083):540-4. Epub Mar. 8, 2006.
Singh et al., Anionic microparticles are a potent delivery system for recombinant antigens from Neisseria meningitidis serotype B. J Pharm Sci. Feb. 2004;93(2):273-82.
Singh et al., Cationic microparticles are an effective delivery system for immune stimulatory cpG DNA. Pharm Res. Oct. 2001;18(10):1476-9.
Singh et al., Nanoparticles and microparticles as vaccine-delivery systems. Expert Rev Vaccines. Oct. 2007;6(5):797-808.
Skeen et al., Regulation of murine macrophage IL-12 production. Activation of macrophages in vivo, restimulation in vitro, and modulation by other cytokines. J Immunol. Feb. 1, 1996;156(3):1196-206.
Sondel et al., Preclinical and clinical development of immunocytokines. Curr Opin Investig Drugs. 2003;4(6):696-700.
Stivaktakis et al., Immune responses in mice of beta-galactosidase adsorbed or encapsulated in poly(lactic acid) and poly(lactic-co-glycolic acid) microspheres. J Biomed Mater Res A. Jun. 1, 2005;73(3):332-8.
Stivaktakis et al., PLA and PLGA microspheres of beta-galactosidase: Effect of formulation factors on protein antigenicity and immunogenicity. J Biomed Mater Res A. Jul. 1, 2004;70(1):139-48.
Storm et al., Surface Modification of Nanoparticles to Oppose Uptake by the Mononuclear Phagocyte System. Adv Drug Deliv Rev. 1995;17:31-48.
Suri et al., Nanotechnology-based drug delivery systems. J Occup Med Toxicol. Dec. 1, 2007;2:16.
Tabata et al., Macrophage activation through phagocytosis of poly (L-lactic acid) microspheres containing an immunomodulatory agent. 1989;7(2):79-86. Abtract only on p. 85-6.
Tabata et al., Protein precoating of polylactide microspheres containing a lipophilic immunopotentiator for enhancement of macrophage phagocytosis and activation. Pharm Res. Apr. 1989;6(4):296-301.
Tarlinton et al., Antigen to the node: B cells go native. Immunity. Apr. 2007;26(4):388-90.
Taylor et al., Macrophage receptors and immune recognition. Annu Rev Immunol. 2005;23:901-44.
Timmerman et al., Carrier protein conjugate vaccines: the "missing link" to improved antibody and Ctl responses? Hum Vaccin. Mar. 2009;5(3):181-3. Epub Mar. 24, 2009.
Tomai et al., Resiquimod and other immune response modifiers as vaccine adjuvants. Expert Rev Vaccines. Oct. 2007;6(5):835-47.
Tong et al., Ring-opening polymerization-mediated controlled formulation of polylactide-drug nanoparticles. J Am Chem Soc. Apr. 8, 2009;131(13):4744-54. E-pub Mar. 12, 2009.
Trindade et al., Nanocrystalline Semiconductors: Synthesis, Properties, and Perspectives. Chem Mat. 2001;13(11):3843-58.
Uhrich et al., Polymeric Systems for Controlled Drug Release. Chem Rev. 1999;99(11):3181-98.
Unkeless et al., Structure and function of human and murine receptors for IgG. Annu Rev Immunol. 1998;6:251-81.
Uwatoku et al., Application of Nanoparticle Technology for the Prevention of Restenosis After Balloon Injury in Rats. Circ Res. 2003;92(7):e62-9.
Van Broekhoven et al., Targeting dendritic cells with antigen-containing liposomes: a highly effective procedure for induction of antitumor immunity and for tumor immunotherapy. Cancer Res. Jun. 15, 2004;64(12):4357-65.

(56) References Cited

OTHER PUBLICATIONS

Vascotto et al., Antigen presentation by B lymphocytes: how receptor signaling directs membrane trafficking. Curr Opin Immunol. 2007;19(1):93-8.
Vauthier et al., Design aspects of poly(alkylcyanoacrylate) nanoparticles for drug delivery. J Drug Target. Dec. 2007;15(10):641-63.
Vollmer et al., Characterization of three CpG oligodeoxynucleotide classes with distinct immunostimulatory activities. Eur J Immunol. Jan. 2004;34(1):251-62.
Von Andrian et al., Homing and cellular traffic in lymph nodes. Nat Rev Immunol. 2003;3(1 1):867-78.
Wang et al., A novel biodegradable gene carrier based on polyphosphoester. J Am Chem Soc. 2001;123(38):9480-1.
Wessels et al., Studies of group B streptococcal infection in mice deficient in complement component C3 or C4 demonstrate an essential role for complement in both innate and acquired immunity. Proc Natl Acad Sci USA. 1995;92(25):11490-4.
Whelan et al., Efficient recovery of infectious vesicular stomatitis virus entirely from cDNA clones. Proc Natl Acad Sci USA. 1995;92(18):8388-92.
Wu et al., A novel chitosan CpG nanoparticle regulates cellular and humoral immunity of mice.Biomed Environ Sci. Apr. 2006;19(2):87-95.
Wu et al., Resiquimod: a new immune response modifier with potential as a vaccine adjuvant for Th1 immune responses. Antiviral Res. Nov. 2004;64(2):79-83.
Yang, Imaging of vascular gene therapy. Radiology. 2003;228:36-49.
Yoo et al., In vitro and in vivo anti-tumor activities of nanoparticles based on doxorubicin-PLGA conjugates. J Control Release. 2000;68(3):419-31.
Yu et al., Potent CpG oligonucleotides containing phosphodiester linkages: in vitro and in vivo immunostimulatory properties. Biochem Biophys Res Commun. Sep. 13, 2002;297(1):83-90.
Yuan et al., Intranasal immunization with chitosan/pCETP nanoparticles inhibits atherosclerosis in a rabbit model of atherosclerosis. Vaccine. Jul. 4, 2008;26(29-30):3727-34. Epub May 16, 2008.
Zauner et al., Polylysine-based transfection systems utilizing receptor-mediated delivery. Adv.Drug Del Rev. 1998;30:97-113.
Zhang et al., A comparative study of the antigen-specific immune response induced by co-delivery of CpG ODN and antigen using fusion molecules or biodegradable microparticles. J Pharm.Sci. Dec. 2007;96(12):3283-92.
Zhang et al., Nanoparticles of poly(lactide)/vitamin E TPGS copolymer for cancer chemotherapy: synthesis, formulation, characterization and in vitro drug release. Biomaterials. Jan. 2006;27(2):262-70.
Zheng et al., Highly fluorescent, water-soluble, size-tunable gold quantum dots. Phys Rev Lett. 2004;93(7):077402.1-4.
Zheng et al., How antigen quantity and quality determine T-cell decisions in lymphoid tissue. Mol Cell Biol. Jun. 2008;28(12):4040-51. Epub Apr. 21, 2008.
Zhou et al., Investigation on a novel core-coated micro spheres protein delivery system. J Control Release. 2001;75(1-2):27-36.
Zwiorek et al., Delivery by cationic gelatin nanoparticles strongly increases the immunostimulatory effects of CpG oligonucleotides. Pharm Res. Mar. 2008;25(3):551-62. Epub Oct. 3, 2007.
Bae et al., Mixed polymeric micelles for combination cancer chemotherapy through the concurrent delivery of multiple chemotherapeutic agents. J Control Release. Oct. 8, 2007;122(3):324-30. Epub Jun. 13, 2007.
Bala et al., PLGA nanoparticles in drug delivery: the state of the art. Crit Rev Ther Drug Carrier Syst. 2004;21(5):387-422.
Barichello et al., Encapsulation of hydrophilic and lipophilic drugs in PLGA nanoparticles by the nanoprecipitation method. Drug Dev Ind Pharm. Apr. 1999;25(4):471-6.
Batista et al., The who, how and where of antigen presentation to B cells. Nat Rev Immunol. Jan. 2009;9(1):15-27.
Bharali, Micro- and Nanoparticles-Based Vaccines for Hepatitis B. Immune-Mediated Diseases. 2007:415-21.
Black et al., Advances in the design and delivery of peptide subunit vaccines with a focus on toll-like receptor agonists. Expert Rev Vaccines. Feb. 2010;9(2):157-73.
Borges et al., Evaluation of the immune response following a short oral vaccination schedule with hepatitis B antigen encapsulated into alginate-coated chitosan nanoparticles. Eur J Pharm Sci. Dec. 2007;32(4-5):278-90. Epub Aug. 15, 2007.
Cameron et al., Aliphatic polyester polymer stars: synthesis, properties and applications in biomedicine and nanotechnology. Chem Soc Rev. Mar. 2011;40(3):1761-76.
Czarniecki, Small molecule modulators of toll-like receptors. J Med Chem. Nov. 13, 2008;51(21):6621-6. doi: 10.1021/jm800957k. Epub Oct. 2, 2008.
Farokhzad et al., Drug delivery systems in urology—getting "smarter". Urology. Sep. 2006;68(3):463-9.
Govender et al., PLGA nanoparticles prepared by nanoprecipitation: drug loading and release studies of a water soluble drug. J Control Release. Feb. 1, 1999;57(2):171-85.
Gvili et al., PLGA nanoparticles for DNA vaccination-waiving complexity and increasing efficiency. Molc Ther. 2006;13:S209.
Haddadi, Delivery of rapamycin by PLGA nanoparticles enhances its suppressive activity on dendritic cells. J Biomed Mat Res A. 2007;84A(4):885-98.
Kim et al., Enhancement of DNA vaccine potency through coadministration of CIITA DNA with DNA vaccines via gene gun. J Immunol. May 15, 2008;180(10):7019-27.
Lamalle-Bernard et al., Coadsorption of HIV-1 p24 and gp120 proteins to surfactant-free anionic PLA nanoparticles preserves antigenicity and immunogenicity. J Control Release. Sep. 28, 2006;115(1):57-67. Epub Jul. 13, 2006.
Lee et al., Adaptations of nanoscale viruses and other protein cages for medical applications. Nanomedicine. Sep. 2006;2(3):137-49.
Lindblad, Aluminium compounds for use in vaccines. Immunol Cell Biol. Oct. 2004;82(5):497-505.
Pitaksuteepong, Nanoparticles: A vaccine adjuvant for subcutaneous administration. Naresuan University J. 2005;13(2):53-62.
Samuel et al, Polymeric nanoparticles for targeted delivery of therapeutic vaccines to dendritic cells. Proc Intl Conf on MEMS, NANO and Smart Sys. Jul. 2003;20-23:242-6.
Sonehara et al., Hexamer palindromic oligonucleotides with 5'-CG-3' motif(s) induce production of interferon. J Interferon Cytokine Res. Oct. 1996;16(10):799-803.
Tang et al., In Vitro Gene Delivery by Degraded Polyamidoamine Dendrimers. Bioconjugate Chem. 1996;7:703-14.
Yang et al., Tumor necrosis factor alpha blocking peptide loaded PEG-PLGA nanoparticles: preparation and in vitro evaluation. Int J Pharm. Feb. 22, 2007;331(1):123-32.
Extended European Search Report for EP 11787447.9 mailed Mar. 5, 2014.

\* cited by examiner

SEQUENCE LISTING

```
<160> NUMBER OF SEQ ID NOS: 2

<210> SEQ ID NO 1
<211> LENGTH: 17
<212> TYPE: PRT
<213> ORGANISM: G. gallus

<400> SEQUENCE: 1

Ile Ser Gln Ala Val His Ala Ala His Ala Glu Ile Asn Glu Ala Gly
1               5                   10                  15
```

Arg

```
<210> SEQ ID NO 2
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 2
tccatgacgt tcctgacgtt                                              20
```

DOSE SELECTION OF ADJUVANTED SYNTHETIC NANOCARRIERS

RELATED APPLICATIONS

This application claims the benefit under 35 U.S.C. §119 of U.S. provisional applications 61/348,713, filed May 26, 2010, 61/348,717, filed May 26, 2010, 61/348,728, filed May 26, 2010, and 61/358,635, filed Jun. 25, 2010, the entire contents of each of which are incorporated herein by reference.

SEQUENCE LISTING

The contents of the ASCII text file entitled "SEQUENCE LISTING ST25", created on Jan. 29, 2013, and 1 kB in size is incorporated herein by reference in its entirety.

BACKGROUND OF THE INVENTION

Adjuvants are important components of the majority of currently used vaccination regimens. They are likely to be integrated into future vaccine products as well. Numerous novel adjuvants are now being developed, and many of those have been demonstrated to augment immune responses to vaccines in research and clinical settings. However, adjuvant doses that are beneficial for immune response augmentation can be capable of inducing side-effects in a significant group of patients. In fact, these two capacities of adjuvants are intrinsically linked since it is the broad immune stimulation per se that provides stimuli for vaccination augmentation as well as its side-effects (toxicities). Both of these processes are known to be driven by release of inflammatory cytokines. Therefore, approaches that diminish side-effects of adjuvant administration and/or specifically augment certain immune responses, will be of great clinical value.

Therefore, what is needed are compositions and methods that effectively provide desired immune response(s) that can reduce the frequency of adverse events associated with adjuvant use in vaccines.

SUMMARY OF THE INVENTION

In one aspect, a method comprising providing a dose of adjuvant and a dose of antigen, wherein at least a portion of the dose of adjuvant is coupled to synthetic nanocarriers, and generating an antibody titer against the antigen through administration of the dose of adjuvant and the dose of antigen to a subject, wherein the dose of adjuvant is less than a separate dose of adjuvant that results in an antibody titer similar to that generated through administration of the dose of adjuvant and the dose of antigen to the subject is provided. In one embodiment, the method further comprises choosing the dose of adjuvant to be less than a separate dose of adjuvant that results in an antibody titer similar to that generated through administration of the dose of adjuvant and the dose of antigen to the subject. Preferably, the same entity performs each of the steps of these methods (i.e., the same entity performs the providing, generating and/or choosing steps). In another aspect, a composition comprising the dose of adjuvant that is less than a separate dose of adjuvant that results in an antibody titer similar to that generated through administration of the dose of adjuvant and the dose of antigen to the subject is provided.

In another aspect, a method comprising providing a dose of adjuvant, wherein at least a portion of the dose of adjuvant is coupled to synthetic nanocarriers, and generating a systemic cytokine release through administration of the dose of adjuvant to a subject, wherein the dose of adjuvant is greater than a separate dose of adjuvant that results in a systemic cytokine release similar to that generated through administration of the dose of adjuvant to the subject is provided. In one embodiment, the method further comprises choosing the dose of adjuvant to be greater than a separate dose of adjuvant that results in a systemic cytokine release similar to that generated through administration of the dose of adjuvant to the subject. Preferably, the same entity performs each of the steps of these methods (i.e., the same entity performs the providing, generating and/or choosing steps). In another aspect, a composition comprising the dose of adjuvant that is greater than a separate dose of adjuvant that results in a systemic cytokine release similar to that generated through administration of the dose of adjuvant to the subject is provided.

In one embodiment, the adjuvant(s) of any of the methods and compositions provided herein comprise an agonist for Toll-Like Receptors 3, 4, 5, 7, 8, or 9 or a combination thereof. In another embodiment, the adjuvant comprises an agonist for Toll-Like Receptors 3, an agonist for Toll-Like Receptors 7 and 8, or an agonist for Toll-Like Receptor 9. In yet another embodiment, the adjuvant comprises R848, immunostimulatory DNA, or immunostimulatory RNA. In a further embodiment, the dose of adjuvant of any of the methods and compositions provided herein comprises two or more types of adjuvants. In one embodiment, a portion of the dose of adjuvant is not coupled to the synthetic nanocarriers.

In another embodiment of any of the methods and compositions provided herein more than one type of antigen are administered to the subject. In one embodiment, at least a portion of the dose of antigen(s) is coupled to the synthetic nanocarriers. In another embodiment, at least a portion of the dose of antigen(s) is not coupled to the synthetic nanocarriers. In yet another embodiment, at least a portion of the dose of antigen(s) is coadministered with the synthetic nanocarriers. In still another embodiment, at least a portion of the dose of antigen(s) is not coadministered with the synthetic nanocarriers. In one embodiment, the antigen(s) comprise a B cell antigen and/or a T cell antigen. In another embodiment, the T cell antigen comprises a universal T cell antigen or T-helper cell antigen. In still another embodiment, the antigen(s) comprise a B cell antigen or a T cell antigen and a universal T cell antigen or T-helper cell antigen. In one embodiment, the T helper cell antigen comprises a peptide obtained or derived from ovalbumin. In another embodiment, the peptide obtained or derived from ovalbumin comprises the sequence as set forth in SEQ ID NO: 1. In still another embodiment of any of the methods and compositions provided herein, the universal T cell antigen or T helper cell antigen is coupled to the synthetic nanocarriers by encapsulation. In yet another embodiment of any of the methods and compositions provided herein, the B cell antigen comprises nicotine. In a further embodiment, the synthetic nanocarriers comprise nicotine and a universal T cell antigen or T helper cell antigen. In still a further embodiment, the nicotine and/or universal T cell antigen or T helper cell antigen are coupled to the synthetic nanocarriers. In one embodiment, the universal T cell antigen or T helper cell antigen is coupled by encapsulation.

In another embodiment of any of the methods and compositions provided, the dose of adjuvant comprises R848 and the dose of antigen comprises nicotine and a universal T cell antigen or T-helper cell antigen, wherein the nicotine and universal T cell antigen or T-helper cell antigen are also coupled to the synthetic nanocarriers, and wherein the synthetic nanocarriers comprise one or more polymers.

In another embodiment of any of the methods and compositions provided herein, the synthetic nanocarriers comprise lipid nanoparticles, polymeric nanoparticles, metallic nanoparticles, surfactant-based emulsions, dendrimers, buckyballs, nanowires, virus-like particles, peptide or protein particles, nanoparticles that comprise a combination of nanomaterials, spheroidal nanoparticles, cuboidal nanoparticles, pyramidal nanoparticles, oblong nanoparticles, cylindrical nanoparticles, or toroidal nanoparticles. In one embodiment, the synthetic nanocarriers comprise one or more polymers. In another embodiment, the one or more polymers comprise a polyester. In yet another embodiment, the one or more polymers comprise or further comprise a polyester coupled to a hydrophilic polymer. In still another embodiment, the polyester comprises a poly(lactic acid), poly(glycolic acid), poly(lactic-co-glycolic acid), or polycaprolactone. In one embodiment, the hydrophilic polymer comprises a polyether. In another embodiment, the polyether comprises polyethylene glycol.

In one embodiment of any of the methods and compositions provided, at least one dosage form comprises the dose of adjuvant. In another embodiment, a vaccine comprises the dosage form(s). In still another embodiment, the more than one dosage form comprise the dose of adjuvant, and the more than one dosage form are co-administered.

In one embodiment of any of the methods provided, the administration is by a route that comprises subcutaneous, intramuscular, intradermal, oral, intranasal, transmucosal, rectal; ophthalmic, transdermal or transcutaneous administration, or a combination thereof.

In another embodiment of any of the methods provided, the subject has cancer, an infectious disease, a non-autoimmune metabolic disease, a degenerative disease, an addiction, and atopic condition, asthma; chronic obstructive pulmonary disease (COPD) or a chronic infection.

In another aspect, a dose of adjuvant and dose of antigen or dose of adjuvant, as defined in regard to any of the methods or compositions provided, for use in therapy or prophylaxis is provided.

In yet another aspect, a dose of adjuvant and dose of antigen or dose of adjuvant, as defined in regard to any of the methods or compositions provided, for use in any of the methods provided is provided.

In still another aspect, a dose of adjuvant and dose of antigen or dose of adjuvant, as defined in regard to any of the methods or compositions provided, for use in a method of treating cancer, an infectious disease, a non-autoimmune metabolic disease, a degenerative disease, an addiction, and atopic condition, asthma; chronic obstructive pulmonary disease (COPD) or a chronic infection is provided. In one embodiment, the method comprises administration of the dose(s) by a route that comprises subcutaneous, intramuscular, intradermal, oral, intranasal, transmucosal, rectal; ophthalmic, transdermal or transcutaneous administration, or a combination thereof.

In a further aspect, a use of a dose of adjuvant and dose of antigen or dose of adjuvant as defined in regard to any of the methods or compositions provided, for the manufacture of a medicament for use in any of the methods provided is provided.

BRIEF DESCRIPTION OF FIGURES

FIG. 1 shows the systemic cytokine production in mice after nanocarrier (NC) inoculation.

DETAILED DESCRIPTION OF THE INVENTION

Figure 1A:
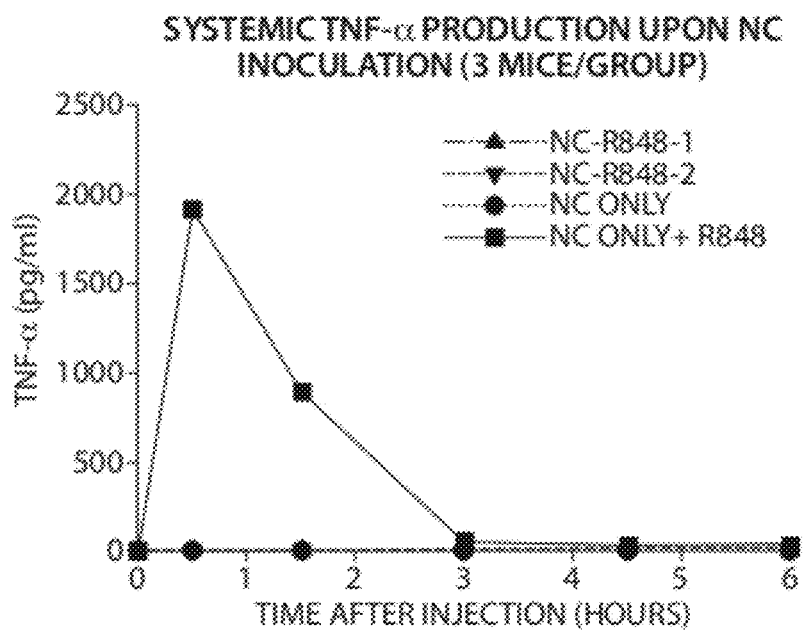
FIGS. 1A, 1B, and 1C show the production of TNF-α, IL-6, and IL-12 in experimental groups, respectively. Sera from groups of three mice were pooled and analyzed by ELISA.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules, reference to "a solvent" includes a mixture of two or more such solvents, reference to "an adhesive" includes mixtures of two or more such materials, and the like.

Introduction

The inventors have unexpectedly and surprisingly discovered that the problems and limitations noted above can be overcome by practicing the invention disclosed herein. The discoveries described herein relate to adjuvant coupling to nanocarriers, and based on these discoveries methods and related compositions are provided that are directed to generating desired immune responses through the selection of specific doses of adjuvant coupled to nanocarriers. In some embodiments, and depending on the desired immune response(s), these doses are less than doses of adjuvant not coupled to nanocarriers in a similar context. In other embodiments, these doses are greater than doses of adjuvant not coupled to nanocarriers.

In one aspect, the inventors have unexpectedly discovered that it is possible to provide methods, and related compositions, that comprise a method comprising administering a dose of adjuvant, when coupled to synthetic nanocarriers, that is less than a separate dose of adjuvant that results in an immune response (e.g., antibody titer) similar to that generated through administration of the dose of adjuvant to a subject. Because of the stronger adjuvant effect as a result of coupling at least a portion of a dose of adjuvant to a synthetic nanocarrier, less adjuvant may be used. The doses of adjuvant, therefore, can be sub-therapeutic or toxicity-reduced doses, wherein at least a portion of the dose of the adjuvant is coupled to synthetic nanocarriers. In another aspect, the invention relates to a composition comprising a dosage form comprising a sub-therapeutic or toxicity-reduced dose of adjuvant, and a pharmaceutically acceptable excipient, wherein at least a portion of the dose of the adjuvant is coupled to synthetic nanocarriers. In still another aspect, the invention relates to a method comprising administering a sub-therapeutic or toxicity-reduced dose of adjuvant to a subject; wherein at least a portion of the dose of the adjuvant is coupled to synthetic nanocarriers.

Coupling of adjuvants to nanocarriers was observed to provide a stronger adjuvant effect and to lead to a substantially higher antibody response when compared to admixed adjuvant. In addition, it was also observed that coupled adjuvant results in a greater antibody response even when a substantially greater amount of free adjuvant (as much as 6-fold greater) is used. See Example 11. This result is contrary to what is expected from the teachings provided in Diwan et al., Current Drug Delivery, 2004, 1, 405-412, where it was found that antibody production, particularly at lower doses of adjuvant, was higher when adjuvant was given in solution rather than with particulate delivery. An opposite result, however, is described herein.

In another aspect, therefore, the inventors have unexpectedly discovered that it is possible to provide methods, and related compositions, that comprise a method comprising providing a dose of adjuvant and a dose of antigen, wherein at least a portion of the dose of adjuvant is coupled to synthetic nanocarriers, and generating an antibody titer against the antigen through administration of the dose of adjuvant and the dose of antigen to a subject, wherein the dose of adjuvant is less than a separate dose of adjuvant that results in an antibody titer similar to that generated through administration of the dose of adjuvant and the dose of antigen to the subject. In embodiments, the method further comprises choosing the dose of adjuvant to be less than a separate dose of adjuvant that results in an antibody titer similar to that generated through administration of the dose of adjuvant and the dose of antigen to the subject (e.g., a human). Preferably, the steps of the methods provided herein are performed by the same entity. In still another aspect, the invention relates to a composition comprising a dosage form comprising a dose of adjuvant and a dose of antigen and a pharmaceutically acceptable excipient, wherein at least a portion of the dose of adjuvant is coupled to synthetic nanocarriers, and wherein the dose of adjuvant is less than a separate dose of adjuvant that results in an antibody titer similar to that generated through administration of the dose of adjuvant and the dose of antigen to a subject.

It has also been demonstrated that coupling of adjuvant to nanocarriers can result in a lower immediate systemic cytokine induction than utilizing free adjuvant. Therefore, coupling of adjuvant to nanocarriers can allow for the use of a higher dose of adjuvant as compared to separate adjuvant. In another aspect, therefore, the invention relates to a method comprising providing a dose of adjuvant, wherein at least a portion of the dose of adjuvant is coupled to synthetic nanocarriers, generating an immune response (e.g., a systemic cytokine release) through administration of the dose of adjuvant to a subject (e.g., a human), wherein the dose of adjuvant is greater than a separate dose of adjuvant that results in the immune response similar to that generated through administration of the dose of adjuvant to the subject. In embodiments, the method further comprises choosing the dose of adjuvant to be greater than a separate dose of adjuvant that results in an immune response (e.g., systemic cytokine release) similar to that generated through administration of the dose of adjuvant to the subject. Preferably, the steps of the methods provided herein are performed by the same entity. In yet another aspect, the invention relates to a composition comprising a dosage form comprising a dose of adjuvant and a pharmaceutically acceptable excipient, wherein at least a portion of the dose of the adjuvant is coupled to synthetic nanocarriers, and wherein the dose of adjuvant is greater than a separate dose of adjuvant that results in an immune response (e.g., systemic cytokine release) similar to that generated through administration of the dose of adjuvant to the subject.

Collectively, with the discoveries provided herein it is now possible to select an adjuvant dose depending on the desired immune result that is specific for the use of adjuvant coupled to nanocarriers. The dose can be a lower one (as compared to separate adjuvant) that generates antibody titers or that avoids unwanted systemic activity (while strongly potentiating local immunostimulatory effects). The dose can be a greater one that generates a similar systemic cytokine release profile as compared to separate adjuvant.

In a further aspect, the administration of compositions provided herein can be beneficial to any subject in which the modulation of an immune response is desired. In some embodiments, the subject is one in which an inflammatory response is desired. In other embodiments, the subjects are those where a Th1 immune response is desired. In some embodiments, the subjects have or are at risk of having cancer. In other embodiments, the subjects have or are at risk of having an infection or an infectious disease. In still other embodiments, the subjects have or are at risk of having an atopic condition, asthma, chronic obstructive pulmonary disease (COPD) or a chronic infection. Methods for the administration of the compositions to such subjects are also provided.

Examples 1-13 illustrates various embodiments of the present invention, including different formulations or aspects of the present invention. The compositions and methods described in the Examples are also provided herein.

The invention will now be described in more detail below.

DEFINITIONS

"Adjuvant" means an agent that does not constitute a specific antigen, but boosts the strength and longevity of immune response to a concomitantly administered antigen. Such adjuvants may include, but are not limited to stimulators of pattern recognition receptors, such as Toll-like receptors, RIG-1 and NOD-like receptors (NLR), mineral salts, such as alum, alum combined with monphosphoryl lipid (MPL) A of Enterobacteria, such as *Escherichia coli, Salmonella minnesota, Salmonella typhimurium*, or *Shigella flexneri* or specifically with MPL® (AS04), MPL A of above-mentioned bacteria separately, saponins, such as QS-21, Quil-A, ISCOMs, ISCOMATRIX™, emulsions such as MF59™, Montanide® ISA 51 and ISA 720, AS02 (QS21+squalene+MPL®), AS15, liposomes and liposomal formulations such as AS01, synthesized or specifically prepared microparticles and microcarriers such as bacteria-derived outer membrane vesicles (OMV) of *N. gonorrheae, Chlamydia trachomatis* and others, or chitosan particles, depot-forming agents, such as Pluronic® block co-polymers, specifically modified or prepared peptides, such as muramyl dipeptide, aminoalkyl glucosaminide 4-phosphates, such as RC529, or proteins, such as bacterial toxoids or toxin fragments.

In embodiments, adjuvants comprise agonists for pattern recognition receptors (PRR), including, but not limited to Toll-Like Receptors (TLRs), specifically TLRs 2, 3, 4, 5, 7, 8, 9 and/or combinations thereof. In other embodiments, adjuvants comprise agonists for Toll-Like Receptors 3, agonists for Toll-Like Receptors 7 and 8, or agonists for Toll-Like Receptor 9; preferably the recited adjuvants comprise imidazoquinolines; such as R848; adenine derivatives, such as those disclosed in U.S. Pat. No. 6,329,381 (Sumitomo Pharmaceutical Company), US Published Patent Application 2010/0075995 to Biggadike et al., or WO 2010/018132 to Campos et al.; immunostimulatory DNA; or immunostimulatory RNA. In specific embodiments, synthetic nanocarriers incorporate as adjuvants compounds that are agonists for toll-like receptors (TLRs) 7 & 8 ("TLR 7/8 agonists"). Of utility are the TLR 7/8 agonist compounds disclosed in U.S. Pat. No. 6,696,076 to Tomai et al., including but not limited to imidazoquinoline amines, imidazopyridine amines, 6,7-fused cycloalkylimidazopyridine amines, and 1,2-bridged imidazoquinoline amines. Preferred adjuvants comprise imiquimod and resiquimod (also known as R848). In specific embodiments, an adjuvant may be an agonist for the DC surface molecule CD40. In certain embodiments, to stimulate immunity rather than tolerance, a synthetic nanocarrier incorporates an adjuvant that promotes DC maturation (needed for priming of naive T cells) and the production of cytokines, such as type I interferons, which promote antibody immune responses. In embodiments, adjuvants also may comprise immunostimulatory RNA molecules, such as but not limited to dsRNA, poly I:C or poly I:poly C12U (available as Ampligen®, both poly I:C and poly I:polyC12U being known as TLR3 stimulants), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some embodiments, an adjuvant may be a TLR-4 agonist, such as bacterial lipopolysaccharide (LPS), VSV-G, and/or HMGB-1. In some embodiments, adjuvants may comprise TLR-5 agonists, such as flagellin, or portions or derivatives thereof, including but not limited to those disclosed in U.S. Pat. Nos. 6,130,082, 6,585,980, and 7,192,725. In specific embodiments, synthetic nanocarriers incorporate a ligand for Toll-like receptor (TLR)-9, such as immunostimulatory DNA molecules comprising CpGs, which induce type I interferon secretion, and stimulate T and B cell activation leading to increased antibody production and cytotoxic T cell responses (Krieg et al., CpG motifs in bacterial DNA trigger direct B cell activation. Nature. 1995. 374:546-549; Chu et al. CpG oligodeoxynucleotides act as adjuvants that switch on T helper 1 (Th1) immunity. J. Exp. Med. 1997. 186:1623-1631; Lipford et al. CpG-containing synthetic oligonucleotides promote B and cytotoxic T cell responses to protein antigen: a new class of vaccine adjuvants. Eur. J. Immunol. 1997. 27:2340-2344; Roman et al. Immunostimulatory DNA sequences function as T helper-1-promoting adjuvants. Nat. Med. 1997. 3:849-854; Davis et al. CpG DNA is a potent enhancer of specific immunity in mice immunized with recombinant hepatitis B surface antigen. J. Immunol. 1998. 160:870-876; Lipford et al., Bacterial DNA as immune cell activator. Trends Microbiol. 1998. 6:496-500; U.S. Pat. No. 6,207,646 to Krieg et al.; U.S. Pat. No. 7,223,398 to Tuck et al.; U.S. Pat. No. 7,250,403 to Van Nest et al.; or U.S. Pat. No. 7,566,703 to Krieg et al.

In some embodiments, adjuvants may be proinflammatory stimuli released from necrotic cells (e.g., urate crystals). In some embodiments, adjuvants may be activated components of the complement cascade (e.g., CD21, CD35, etc.). In some embodiments, adjuvants may be activated components of immune complexes. The adjuvants also include complement receptor agonists, such as a molecule that binds to CD21 or CD35. In some embodiments, the complement receptor agonist induces endogenous complement opsonization of the synthetic nanocarrier. In some embodiments, adjuvants are cytokines, which are small proteins or biological factors (in the range of 5 kD-20 kD) that are released by cells and have specific effects on cell-cell interaction, communication and behavior of other cells. In some embodiments, the cytokine receptor agonist is a small molecule, antibody, fusion protein, or aptamer.

In embodiments, at least a portion of the dose of adjuvant is coupled to synthetic nanocarriers, preferably, all of the dose of adjuvant is coupled to synthetic nanocarriers. In embodiments, the dose of adjuvant comprises two or more types of adjuvants. For instance, and without limitation, adjuvants that act on different receptors, such as different TLR receptors may be combined. As an example, in an embodiment a TLR 7/8 agonist may be combined with a TLR 9 agonist. In another embodiment, a TLR 7/8 agonist may be combined with a TLR 4 agonist. In yet another embodiment, a TLR 9 agonist may be combined with a TLR 3 agonist.

"Administering" or "administration" means providing a substance to a subject in a manner that is pharmacologically useful.

"Amount effective" is any amount of a composition that produces one or more desired immune responses. This amount can be for in vitro or in vivo purposes. For in vivo purposes, the amount can be one that a clinician would believe may have a clinical benefit for a subject in need of an immune response. Such subjects include those that have or are at risk of having cancer, an infection or infectious disease, an atopic condition, asthma, chronic obstructive pulmonary disease (COPD) or a chronic infection.

Amounts effective include those that involve the generation of an antibody titer and/or the systemic release of one or more cytokines. In embodiments, the amounts effective include those that involve the production of a systemic cytokine release profile. In some embodiments, the one or more cytokines or cytokine release profile comprises the systemic release of TNF-α, IL-6 and/or IL-12. In other embodiments, the one or more cytokines or cytokine release profile comprises the systemic release of IFN-γ, IL-12 and/or IL-18. This can be monitored by routine methods. An amount that is effective to produce one or more desired immune responses can also be an amount of a composition provided herein that produces a desired therapeutic endpoint or a desired therapeutic result.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a "maximum dose" be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In embodiments, the selection of the doses of adjuvant(s) coupled to nanocarriers is dependent on a comparison with doses of separate adjuvant(s) (i.e., not coupled to nanocarriers) that generate a similar immune response (with or without antigen). As used herein, a "similar immune response" includes immune responses that a health practitioner would expect to result in a comparable therapeutic result in a subject. Similar immune responses also include immune responses that are the same type of response (e.g., the induction of the same particular cytokine or set of cytokines, the generation of the same type of antibody titer, etc.), the level of which is not considered to be statistically different.

Whether or not a similar immune response is generated can be determined with in vitro or in vivo techniques. For example, whether or not a similar immune response is generated can be determined by measuring an immune response (e.g., antibody titer or cytokine(s) release) in a subject through the administration of the dose of separate adjuvant (with or without antigen) to the subject. The subject is not necessarily the same subject to which the inventive composition comprising nanocarrier coupled adjuvant are administered in the inventive methods. The subject, for example, can be a clinical trial subject or subjects to which the dose of separate adjuvant was previously administered. The subject can also be an animal model subject or subjects to which the dose of separate adjuvant was previously administered. The determination of the immune response in the subject can also be determined by measuring the response of cells isolated from the subject, or cells from another subject or subjects, that are placed in contact with the dose of separate adjuvant (with or without antigen). The other subject or subjects again can be previous clinical trial subjects or animal model subjects.

In embodiments, the comparison is based on the measurement of an immune response (e.g., particular type of antibody titer, particular cytokine level, levels of a set of cytokines) can be done within the first 1, 2, 3, 4, 5, 6, 7, 8, 9, 10, 12, 15, 17, 20, 25, 30, 35, 40 or more hours after immunization with the dose of separate adjuvant. In other embodiments, the immune response is measured within 1, 2, 3, 4, 5, 6, 7, 8, 9, 10, 12, 15, 20, 25, 30, 35, 40 or more days after immunization. Assays for determining whether or not an immune response is similar are known to those of ordinary skill in the art. Additionally, examples of such assays are described in more detail in the Examples.

Whether or not a dose of separate adjuvant (with or without antigen) generates a similar immune response can also be determined by what a health practitioner would expect the immune response (or level of immune response) to be based on results from prior in vitro and/or in vivo assays (in other subjects). Such results can include results from clinical trials where effective doses have been determined. Accordingly, the dose of separate adjuvant that is used in the comparison is an amount a health practitioner would expect to be effective to produce the immune response or therapeutic effect. In another embodiment, the dose of separate adjuvant that is used in the comparison is the dose of separate adjuvant a health practitioner would expect to be the maximum tolerated dose. In embodiments, the dose of coupled adjuvant is 1-fold, 2-fold, 3-fold, 4-fold, 5-fold or 6-fold less than a dose of separate adjuvant that is an amount effective to generate an immune response or therapeutic result provided herein. In other embodiments, the dose of coupled adjuvant is at least 1-fold, 2-fold, 3-fold, 4-fold, 5-fold or 6-fold less than a dose of separate adjuvant that is a maximum tolerated dose. In other embodiments, the dose of coupled adjuvants is greater than a dose of separate adjuvant that is an amount effective to generate an immune response or therapeutic result provided herein. In other embodiments, the dose of coupled adjuvant is greater than a dose of separate adjuvant that is a maximum tolerated dose.

In general, doses of the adjuvant(s) or antigen(s) of the compositions of the invention can range from about 0.001 µg/kg to about 100 mg/kg. In some embodiments, the doses can range from about 0.01 µg/kg to about 10 mg/kg. In still other embodiments, the doses can range from about 0.1 µg/kg to about 5 mg/kg, about 1 µg/kg to about 1 mg/kg, about 10 µg/kg to about 0.5 mg/kg or about 100 µg/kg to about 0.5 mg/kg. In further embodiments, the doses can range from about 0.1 µg/kg to about 100 µg/kg. In still further embodiments, the doses can range from about 30 µg/kg to about 300 µg/kg. Alternatively, the dose can be administered based on the number of synthetic nanocarriers. For example, useful doses include greater than $10^6$, $10^7$, $10^8$, $10^9$ or $10^{10}$ synthetic nanocarriers per dose. Other examples of useful doses include from about $1\times10^6$ to about $1\times10^{10}$, about $1\times10^7$ to about $1\times10^9$ or about $1\times10^8$ to about $1\times10^9$ synthetic nanocarriers per dose.

In embodiments, the dose is a "sub-therapeutic dose", which means an amount (e.g. specified number of mass units) of an adjuvant (or adjuvants) that provides a desired therapeutic outcome wherein the sub-therapeutic dose is an amount which is numerically less than would be required to provide substantially the same therapeutic outcome if administered separately. In this context, "separate" or "separately" means that adjuvant (or adjuvants) is not coupled to a synthetic nanocarrier. In an embodiment, the sub-therapeutic dose of R848 comprises from 0.01 micrograms/kg to 100 micrograms/kg, preferably 0.1 micrograms/kg to 10 micrograms/kg, of R848. In an embodiment, the sub-therapeutic dose of CpG containing oligonucleotide comprises from 0.001 µg/kg to 2 mg/kg, preferably from about 0.01 µg/kg to 0.1 mg/kg, of CpG containing oligonucleotide. In yet another embodiment, the sub-therapeutic dose of an immunologically active nucleic acid or a derivative thereof comprises from 0.001 µg/kg to 2 mg/kg, preferably from 0.01 µg/kg to 0.1 mg/kg. In another embodiment, a sub-therapeutic dose of MPL® comprises from 0.001 µg/kg to 0.5 mg/kg.

In other embodiments, the dose is a "toxicity-reduced dose", which means a dose of an adjuvant that provides a particular systemic cytokine release, preferably a particular systemic cytokine release profile, wherein the toxicity-reduced dose is greater than a dose of adjuvant that would be required to provide substantially the same particular systemic cytokine release, preferably a particular systemic cytokine release profile, when administered separately. In this context, "separately" means adjuvant that is not coupled to a synthetic nanocarrier. Additionally, "systemic cytokine release profile" means a pattern of systemic cytokine release, wherein the pattern comprises cytokine levels measured for several different systemic cytokines. In an embodiment, the toxicity-reduced dose of R848 comprises from 0.01 micrograms/kg to 100 micrograms/kg, preferably 0.1 micrograms/kg to 10 micrograms/kg, of R848. In an embodiment, the toxicity-reduced dose of CpG containing oligonucleotide comprises from 0.001 micrograms/kg to 2 mg/kg, preferably 0.01 μg/kg micrograms to 0.1 mg/kg, of CpG containing oligonucleotide. In another embodiment, sub-therapeutic dose of MPL® comprises from 0.001 μg/kg to 0.5 mg/kg.

"Antibody response" means any immune response that results in the production or stimulation of B cells and/or the production of antibodies. "Antibody titer" means the production of a measurable level of antibodies. Preferably, the antibody response or generation of the antibody titer is in a human. In some embodiments, the antibodies are antibodies of a certain isotype, such as IgG or a subclass thereof. Methods for measuring antibody titers are known in the art and include Enzyme-linked Immunosorbent Assay (ELISA). Methods for measuring antibody titers are also described in some detail in the Examples. Preferably, the antibody response or antibody titer is specific to an antigen. Such antigen can be coadministered with the adjuvant coupled nanocarrier but can also not be coadministered.

"Antigen" means a B cell antigen or T cell antigen. In embodiments, antigens are coupled to the synthetic nanocarriers. In other embodiments, antigens are not coupled to the synthetic nanocarriers. In embodiments antigens are coadministered with the synthetic nanocarriers. In other embodiments antigens are not coadministered with the synthetic nanocarriers. "Type(s) of antigens" means molecules that share the same, or substantially the same, antigenic characteristics. In embodiments, antigens of the compositions provided are associated with the disease or condition that is being treated. For example, the antigen can be an allergen (for the treatment of an allergy or allergic condition), a cancer-associated antigen (for the treatment of cancer or a tumor), an infectious agent antigen (for the treatment of an infection, an infectious disease or a chronic infectious disease), etc.

"At least a portion of the dose" means at least some part of the dose, ranging up to including all of the dose.

An "at risk" subject is one in which a health practitioner believes has a chance of having a disease or condition as provided herein.

"B cell antigen" means any antigen that is recognized by a B cell, and triggers an immune response in a B cell (e.g., an antigen that is specifically recognized by a B cell receptor on a B cell). In some embodiments, an antigen that is a T cell antigen is also a B cell antigen. In other embodiments, the T cell antigen is not also a B cell antigen. B cell antigens include, but are not limited to, proteins, peptides, small molecules, and carbohydrates. In some embodiments, the B cell antigen comprises a non-protein antigen (i.e., not a protein or peptide antigen). In some embodiments, the B cell antigen comprises a carbohydrate associated with an infectious agent. In some embodiments, the B cell antigen comprises a glycoprotein or glycopeptide associated with an infectious agent. The infectious agent can be a bacterium, virus, fungus, protozoan, parasite or prion. In some embodiments, the B cell antigen comprises a poorly immunogenic antigen. In some embodiments, the B cell antigen comprises an abused substance or a portion thereof. In some embodiments, the B cell antigen comprises an addictive substance or a portion thereof. Addictive substances include, but are not limited to, nicotine, a narcotic, a cough suppressant, a tranquilizer, and a sedative. In some embodiments, the B cell antigen comprises a toxin, such as a toxin from a chemical weapon or natural source, or a pollutant. The B cell antigen may also comprise a hazardous environmental agent. In other embodiments, the B cell antigen comprises an alloantigen, an allergen, a contact sensitizer, a degenerative disease antigen, a hapten, an infectious disease antigen, a cancer antigen, an atopic disease antigen, an autoimmune disease antigen, an addictive substance, a xenoantigen, or a metabolic disease enzyme or enzymatic product thereof.

"Choosing" means making a selection either directly oneself or indirectly, such as, but not limited to, an unrelated third party that takes an action through reliance on one's words or deeds. Generally, the same entity (e.g., individual, group of individuals acting in concert, or organization) provides a composition provided herein and generates the desired immune response through administration of the composition after also selecting the appropriate dose of the composition.

"Coadministered" means administering two or more substances to a subject in a manner that is correlated in time, preferably sufficiently correlated in time so as to provide a modulation in an immune response. In embodiments, coadministration may occur through administration of two or more substances in the same dosage form. In other embodiments, coadministration may encompass administration of two or more substances in different dosage forms, but within a specified period of time, preferably within 1 month, more preferably within 1 week, still more preferably within 1 day, and even more preferably within 1 hour.

"Couple" or "Coupled" or "Couples" (and the like) means to chemically associate one entity (for example a moiety) with another. In some embodiments, the coupling is covalent, meaning that the coupling occurs in the context of the presence of a covalent bond between the two entities. In non-covalent embodiments, the non-covalent coupling is mediated by non-covalent interactions including but not limited to charge interactions, affinity interactions, metal coordination, physical adsorption, host-guest interactions, hydrophobic interactions, π stacking interactions, hydrogen bonding interactions, van der Waals interactions, magnetic interactions, electrostatic interactions, dipole-dipole interactions, and/or combinations thereof. In embodiments, encapsulation is a form of coupling. In embodiments, at least a portion of a dose of adjuvant(s) is coupled to synthetic nanocarriers, preferably all of a dose of adjuvant(s) is coupled to synthetic nanocarriers. In embodiments, at least a portion of a dose of adjuvant(s) is not coupled to synthetic nanocarriers.

"Dosage form" means a pharmacologically and/or immunologically active material in a medium, carrier, vehicle, or device suitable for administration to a subject. In embodiments, at least one inventive dosage form can comprise a dose of an adjuvant or multiple adjuvants. In embodiments, more than one dosage form comprise a dose of adjuvant, preferably in such embodiments the more than one dosage forms are co-administered.

"Encapsulate" means to enclose within a synthetic nanocarrier, preferably enclose completely within a synthetic nanocarrier. Most or all of a substance that is encapsulated is not exposed to the local environment external to the synthetic nanocarrier. Encapsulation is distinct from absorption, which places most or all of a substance on a surface of a synthetic nanocarrier, and leaves the substance exposed to the local environment external to the synthetic nanocarrier.

"Generating" means causing an action, such as an antibody titer against an antigen or systemic cytokine release, to occur, either directly oneself or indirectly, such as, but not limited to, an unrelated third party that takes an action through reliance on one's words or deeds.

An "infection" or "infectious disease" is any condition or disease caused by a microorganism, pathogen or other agent, such as a bacterium, fungus, prion or virus.

"Isolated nucleic acid" means a nucleic acid that is separated from its native environment and present in sufficient quantity to permit its identification or use. An isolated nucleic acid may be one that is (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. Any of the nucleic acids provided herein may be isolated. In some embodiments, the antigens in the compositions provided herein are present in the form of an isolated nucleic acid, such as an isolated nucleic acid that encodes an antigenic peptide, polypeptide or protein.

"Isolated peptide, polypeptide or protein" means the polypeptide (or peptide or protein) is separated from its native environment and present in sufficient quantity to permit its identification or use. This means, for example, the polypeptide (or peptide or protein) may be (i) selectively produced by expression cloning or (ii) purified as by chromatography or electrophoresis. Isolated peptides, proteins or polypeptides may be, but need not be, substantially pure. Because an isolated peptide, polypeptide or protein may be admixed with a pharmaceutically acceptable carrier in a pharmaceutical preparation, the polypeptide (or peptide or protein) may comprise only a small percentage by weight of the preparation. The polypeptide (or peptide or protein) is nonetheless isolated in that it has been separated from the substances with which it may be associated in living systems, i.e., isolated from other proteins (or peptides or polypeptides). Any of the peptides, polypeptides or proteins provided herein may be isolated. In some embodiments, the antigens in the compositions provided herein are in the form of peptides, polypeptides or proteins.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheriodal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 µm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of inventive synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 1000:1, still preferably from 1:1 to 100:1, and yet more preferably from 1:1 to 10:1. Preferably, a maximum dimension of at least 75%, preferably at least 80%, more preferably at least 90%, of the synthetic nanocarriers in a sample, based on the total number of synthetic nanocarriers in the sample is equal to or less than 3 µm, more preferably equal to or less than 2 µm, more preferably equal to or less than 1 µm, more preferably equal to or less than 800 nm, more preferably equal to or less than 600 nm, and more preferably still equal to or less than 500 nm. In preferred embodiments, a maximum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120, more preferably equal to or greater than 130 nm, more preferably equal to or greater than 140 nm, and more preferably still equal to or greater than 150 nm. Measurement of synthetic nanocarrier sizes is obtained by suspending the synthetic nanocarriers in a liquid (usually aqueous) media and using dynamic light scattering (e.g. using a Brookhaven ZetaPALS instrument).

"Pharmaceutically acceptable carrier or excipient" means a pharmacologically inactive material used together with the recited synthetic nanocarriers to formulate the inventive compositions. Pharmaceutically acceptable carriers or excipients comprise a variety of materials known in the art, including but not limited to, saccharides (such as glucose, lactose and the like), preservatives such as antimicrobial agents, reconstitution aids, colorants, saline (such as phosphate buffered saline) and buffers. In some embodiments, pharmaceutically acceptable carriers or excipients comprise calcium carbonate, calcium phosphate, various diluents, various sugars and types of starch, cellulose derivatives, gelatin, vegetable oils and polyethylene glycols.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In embodiments, inventive synthetic nanocarriers do not comprise chitosan.

A synthetic nanocarrier can be, but is not limited to, one or a plurality of lipid-based nanoparticles (e.g. liposomes) (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces, including but not limited to internal surfaces (surfaces generally facing an interior portion of the synthetic nanocarrier) and external surfaces (surfaces generally facing an external environment of the synthetic nanocarrier). Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (4) the lithographically constructed nanoparticles of Published US Patent Application 20090028910 to DeSimone et al., (5) the disclosure of WO 2009/051837 to von Andrian et al., or (6) the nanoparticles disclosed in Published US Patent Application 2008/0145441 to Penades et al.

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers may possess an aspect ratio greater than 1:1, 1:1.2, 1:1.5, 1:2, 1:3, 1:5, 1:7, or greater than 1:10.

"Systemic cytokine release" means the systemic release of one or more particular cytokines. In some embodiments, the systemic cytokine release is a particular systemic cytokine release profile. In some embodiments, the particular systemic cytokine release, preferably a particular systemic cytokine release profile, is in a human. In embodiments, the compositions and methods provided herein (where at least a portion of a dose of adjuvant is coupled to nanocarriers result in a particular systemic cytokine release profile in a subject). The term "separate" or "separately" is also used to mean adjuvant that is not coupled to any synthetic nanocarriers. Additionally, "systemic cytokine release profile" means a pattern of systemic cytokine release, wherein the pattern comprises cytokine levels measured for several different systemic cytokines. In some embodiments, the particular systemic cytokine release profile comprises the systemic release of TNF-α, IL-6 and/or IL-12. In other embodiments, the particular systemic cytokine release profile comprises the systemic release of IFN-γ, IL12 and/or IL-18.

"T cell antigen" means any antigen that is recognized by and triggers an immune response in a T cell (e.g., an antigen that is specifically recognized by a T cell receptor on a T cell or an NKT cell via presentation of the antigen or portion thereof bound to a Class I or Class II major histocompatability complex molecule (MHC), or bound to a CD1 complex.) In some embodiments, an antigen that is a T cell antigen is also a B cell antigen. In other embodiments, the T cell antigen is not also a B cell antigen. T cell antigens generally are proteins, polypeptides or peptides. T cell antigens may be an antigen that stimulates a CD8+ T cell response, a CD4+ T cell response, or both. The nanocarriers, therefore, in some embodiments can effectively stimulate both types of responses.

In some embodiments the T cell antigen is a 'universal' T cell antigen, or T cell memory antigen, (i.e., one to which a subject has a pre-existing memory and that can be used to boost T cell help to an unrelated antigen, for example an unrelated B cell antigen). Universal T cell antigens include tetanus toxoid, as well as one or more peptides derived from tetanus toxoid, Epstein-Barr virus, or influenza virus. Universal T cell antigens also include a components of influenza virus, such as hemagglutinin, neuraminidase, or nuclear protein, or one or more peptides derived therefrom. In some embodiments, the universal T cell antigen is not one that is presented in a complex with a MHC molecule. In some embodiments, the universal T cell antigen is not complexed with a MHC molecule for presentation to a T helper cell. Accordingly, in some embodiments, the universal T cell antigen is not a T helper cell antigen. However, in other embodiments, the universal T cell antigen is a T helper cell antigen.

In embodiments, a T-helper cell antigen may comprise one or more peptides obtained or derived from tetanus toxoid, Epstein-Barr virus, influenza virus, respiratory syncytial virus, measles virus, mumps virus, rubella virus, cytomegalovirus, adenovirus, diphtheria toxoid, or a PADRE peptide (known from the work of Sette et al. U.S. Pat. No. 7,202,351). In other embodiments, a T-helper cell antigen may comprise ovalbumin or a peptide obtained or derived therefrom. Preferably, the ovalbumin comprises the amino acid sequence as set forth in Accession No. AAB59956, NP_990483.1, AAA48998, or CAA2371. In other embodiments, the peptide obtained or derived from ovalbumin comprises the following amino acid sequence: H-Ile-Ser-Gln-Ala-Val-His-Ala-Ala-His-Ala-Glu-Ile-Asn-Glu-Ala-Gly-Arg-OH (SEQ ID NO: 1). In other embodiments, a T-helper cell antigen may comprise one or more lipids, or glycolipids, including but not limited to: α-galactosylceramide (α-GalCer), α-linked glycosphingolipids (from *Sphingomonas* spp.), galactosyl diacylglycerols (from *Borrelia burgdorferi*), lypophosphoglycan (from *Leishmania donovani*), and phosphatidylinositol tetramannoside (PIM4) (from *Mycobacterium leprae*). For additional lipids and/or glycolipids useful as T-helper cell antigen, see V. Cerundolo et al., "Harnessing invariant NKT cells in vaccination strategies." Nature Rev Immun, 9:28-38 (2009).

In embodiments, CD4+ T-cell antigens may be derivatives of a CD4+ T-cell antigen that is obtained from a source, such as a natural source. In such embodiments, CD4+ T-cell antigen sequences, such as those peptides that bind to MHC II, may have at least 70%, 80%, 90%, or 95% identity to the antigen obtained from the source. In embodiments, the T cell antigen, preferably a universal T cell antigen or T-helper cell antigen, may be coupled to, or uncoupled from, a synthetic nanocarrier. In some embodiments, the universal T cell antigen or T-helper cell antigen is encapsulated in the synthetic nanocarriers of the inventive compositions.

"Vaccine" means a composition of matter that improves the immune response to a particular pathogen or disease. A vaccine typically contains factors that stimulate a subject's immune system to recognize a specific antigen as foreign and eliminate it from the subject's body. A vaccine also establishes an immunologic 'memory' so the antigen will be quickly recognized and responded to if a person is re-challenged. Vaccines can be prophylactic (for example to prevent future infection by any pathogen), or therapeutic (for example a vaccine against a tumor specific antigen for the treatment of cancer or against an antigen derived from an infectious agent for the treatment of an infection or infectious disease). In embodiments, a vaccine may comprise dosage forms according to the invention. Preferably, in some embodiments, the vaccines comprise an adjuvant (or adjuvants) coupled to a synthetic nanocarrier.

In specific embodiments, the inventive compositions incorporate adjuvants that comprise agonists for toll-like receptors (TLRs) 7 & 8 ("TLR 7/8 agonists"). Of utility are the TLR 7/8 agonist compounds disclosed in U.S. Pat. No. 6,696,076 to Tomai et al., including but not limited to imidazoquinoline amines, imidazopyridine amines, 6,7-fused cycloalkylimidazopyridine amines, and 1,2-bridged imidazoquinoline amines. Preferred adjuvants comprise imiquimod and R848.

In specific embodiments, the inventive compositions incorporate adjuvants that comprise a ligand for Toll-like receptor (TLR)-9, such as immunostimulatory DNA molecules comprising CpGs, which induce type I interferon secretion, and stimulate T and B cell activation leading to increased antibody production and cytotoxic T cell responses (Krieg et al., CpG motifs in bacterial DNA trigger direct B cell activation. Nature. 1995. 374:546-549; Chu et al. CpG oligodeoxynucleotides act as adjuvants that switch on T helper 1 (Th1) immunity. J. Exp. Med. 1997. 186:1623-1631; Lipford et al. CpG-containing synthetic oligonucleotides promote B and cytotoxic T cell responses to protein antigen: a new class of vaccine adjuvants. Eur. J. Immunol. 1997. 27:2340-2344; Roman et al. Immunostimulatory DNA sequences function as T helper-1-promoting adjuvants. Nat. Med. 1997. 3:849-854; Davis et al. CpG DNA is a potent enhancer of specific immunity in mice immunized with recombinant hepatitis B surface antigen. J. Immunol. 1998. 160:870-876; Lipford et al., Bacterial DNA as immune cell activator. Trends Microbiol. 1998. 6:496-500. In embodiments, CpGs may comprise modifications intended to enhance stability, such as phosphorothioate linkages, or other modifications, such as modified bases. See, for example, U.S. Pat. No. 5,663,153, 6,194,388, 7,262,286, or 7,276,489. In certain embodiments, to stimulate immunity rather than tolerance, a composition provided herein incorporates an adjuvant that promotes DC maturation (needed for priming of naive T cells) and the production of cytokines, such as type I interferons, which promote antibody responses and anti-viral immunity. In some embodiments, the adjuvant comprises a TLR-4 agonist, such as bacterial lipopolysaccharide (LPS), VSV-G, and/or HMGB-1. In some embodiments, adjuvants comprise cytokines, which are small proteins or biological factors (in the range of 5 kD-20 kD) that are released by cells and have specific effects on cell-cell interaction, communication and behavior of other cells. In some embodiments, adjuvants comprise proinflammatory stimuli released from necrotic cells (e.g., urate crystals). In some embodiments, adjuvants comprise activated components of the complement cascade (e.g., CD21, CD35, etc.). In some embodiments, adjuvants comprise activated components of immune complexes. The adjuvants also include those that comprise complement receptor agonists, such as a molecule that binds to CD21 or CD35. In some embodiments, the complement receptor agonist induces endogenous complement opsonization of the nanocarrier. Adjuvants also include those that comprise cytokine receptor agonists, such as a cytokine.

In some embodiments, the cytokine receptor agonist is a small molecule, antibody, fusion protein, or aptamer. In embodiments, adjuvants also may comprise immunostimulatory RNA molecules, such as but not limited to dsRNA or poly I:C (a TLR3 stimulant), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2.

In some embodiments, the adjuvants comprise gel-type adjuvants (e.g., aluminum hydroxide, aluminum phosphate, calcium phosphate, etc.), microbial adjuvants (e.g., immunomodulatory DNA sequences that include CpG motifs; immunostimulatory RNA molecules; endotoxins such as monophosphoryl lipid A; exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.), and/or combinations thereof.

Inventive Compositions

A wide variety of synthetic nanocarriers can be used according to the invention. In some embodiments, synthetic nanocarriers are spheres or spheroids. In some embodiments, synthetic nanocarriers are flat or plate-shaped. In some embodiments, synthetic nanocarriers are cubes or cuboidal. In some embodiments, synthetic nanocarriers are ovals or ellipses. In some embodiments, synthetic nanocarriers are cylinders, cones, or pyramids.

In some embodiments, it is desirable to use a population of synthetic nanocarriers that is relatively uniform in terms of size, shape, and/or composition so that each synthetic nanocarrier has similar properties. For example, at least 80%, at least 90%, or at least 95% of the synthetic nanocarriers, based on the total number of synthetic nanocarriers, may have a minimum dimension or maximum dimension that falls within 5%, 10%, or 20% of the average diameter or average dimension of the synthetic nanocarriers. In some embodiments, a population of synthetic nanocarriers may be heterogeneous with respect to size, shape, and/or composition.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g. a polymeric core) and the shell is a second layer (e.g. a lipid bilayer or monolayer). Synthetic nanocarriers may comprise a plurality of different layers.

In some embodiments, synthetic nanocarriers may optionally comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a core comprising a polymeric matrix surrounded by a lipid layer (e.g., lipid bilayer, lipid monolayer, etc.). In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In some embodiments, synthetic nanocarriers can comprise one or more polymers or polymeric matrices. In some embodiments, such a polymer or polymeric matrix can be surrounded by a coating layer (e.g., liposome, lipid monolayer, micelle, etc.). In some embodiments, various elements of the synthetic nanocarriers can be coupled with the polymer or polymeric matrix.

In some embodiments, an element, such as an immunofeature surface, targeting moiety, antigen, adjuvant, and/or oligonucleotide can be covalently associated with a polymeric matrix. In some embodiments, covalent association is mediated by a linker. In some embodiments, an element can be noncovalently associated with a polymeric matrix. For example, in some embodiments, an element can be encapsulated within, surrounded by, and/or dispersed throughout a polymeric matrix. Alternatively or additionally, an element can be associated with a polymeric matrix by hydrophobic interactions, charge interactions, van der Waals forces, etc.

A wide variety of polymers and methods for forming polymeric matrices therefrom are known conventionally. In general, a polymeric matrix comprises one or more polymers. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

Examples of polymers suitable for use in the present invention include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g., poly(β-hydroxyalkanoate)), poly(orthoesters), polycyanoacrylates, polyvinyl alcohols, polyurethanes, polyphosphazenes, polyacrylates, polymethacrylates, polyureas, polystyrenes, polyamines, polylysine, polylysine-PEG copolymers, and poly(ethyleneimine), poly(ethylene imine)-PEG copolymers.

In some embodiments, polymers in accordance with the present invention include polymers which have been approved for use in humans by the U.S. Food and Drug Administration (FDA) under 21 C.F.R. §177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated (e.g. coupled) within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly (ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In embodiments, the inventive synthetic nanocarriers may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that inventive synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some embodiments, the synthetic nanocarriers comprise one or more polymers. The polymeric synthetic nanocarriers, therefore, can also include those described in WO publication WO2009/051837 by Von Andrian et al., including, but not limited to those, with one or more hydrophilic components. Preferably, the one or more polymers comprise a polyester, such as a poly(lactic acid), poly(glycolic acid), poly(lactic-co-glycolic acid), or polycaprolactone. More preferably, the one or more polymers comprise or further comprise a polyester coupled to a hydrophilic polymer, such as a polyether. In embodiments, the polyether comprises polyethylene glycol. Still more preferably, the one or more polymers comprise a polyester and a polyester coupled to a hydrophilic polymer, such as a polyether. In other embodiments, the one or more polymers are coupled to one or more antigens and/or one or more adjuvants. In embodiments, at least some of the polymers are coupled to the antigen(s) and/or at least some of the polymers are coupled to the adjuvant(s). Preferably, when there are more than one type of polymer, one of the types of polymer is coupled to the antigen(s). In embodiments, one of the other types of polymer is coupled to the adjuvant(s). For example, in embodiments, when the nanocarriers comprise a polyester and a polyester coupled to a hydrophilic polymer, such as a polyether, the polyester is coupled to the adjuvant, while the polyester coupled to the hydrophilic polymer, such as a polyether, is coupled to the antigen(s). In embodiments, where the nanocarriers comprise a T helper cell antigen, the T helper cell antigen can be encapsulated in the nanocarrier.

In some embodiments, synthetic nanocarriers may not comprise a polymeric component. In some embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyl-triethylammonium (DOTMA); dioleoylphosphatidylcholine; cholesterol; cholesterol ester; diacylglycerol; diacylglycerol-succinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, starch, hydroxyethylstarch, carageenan, glycon, amylose, chitosan, N,O-carboxylmethylchitosan, algin and alginic acid, starch, chitin, heparin, inulin, konjac, glucommannan, pustulan, heparin, hyaluronic acid, curdlan, and xanthan. In embodiments, the inventive synthetic nanocarriers do not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

Compositions according to the invention comprise inventive synthetic nanocarriers in combination with pharmaceutically acceptable excipients, such as preservatives, buffers, saline, or phosphate buffered saline. The compositions may be made using conventional pharmaceutical manufacturing and compounding techniques to arrive at useful dosage forms. In an embodiment, inventive synthetic nanocarriers are suspended in sterile saline solution for injection together with a preservative.

In embodiments, when preparing synthetic nanocarriers as carriers for agents (e.g., antigen or adjuvant) for use in vaccines, methods for coupling the agents to the synthetic nanocarriers may be useful. If the agent is a small molecule it may be of advantage to attach the agent to a polymer prior to the assembly of the synthetic nanocarriers. In embodiments, it may also be an advantage to prepare the synthetic nanocarriers with surface groups that are used to couple the agent to the synthetic nanocarrier through the use of these surface groups rather than attaching the agent to a polymer and then using this polymer conjugate in the construction of synthetic nanocarriers. A variety of reactions can be used for the purpose of attaching agents to synthetic nanocarriers.

In certain embodiments, the coupling can be a covalent linker. In embodiments, peptides according to the invention can be covalently coupled to the external surface via a 1,2,3-triazole linker formed by the 1,3-dipolar cycloaddition reaction of azido groups on the surface of the nanocarrier with antigen or adjuvant containing an alkyne group or by the 1,3-dipolar cycloaddition reaction of alkynes on the surface of the nanocarrier with antigens or adjuvants containing an azido group. Such cycloaddition reactions are preferably performed in the presence of a Cu(I) catalyst along with a suitable Cu(I)-ligand and a reducing agent to reduce Cu(II) compound to catalytic active Cu(I) compound. This Cu(I)-catalyzed azide-alkyne cycloaddition (CuAAC) can also be referred as the click reaction.

Additionally, the covalent coupling may comprise a covalent linker that comprises an amide linker, a disulfide linker, a thioether linker, a hydrazone linker, a hydrazide linker, an imine or oxime linker, an urea or thiourea linker, an amidine linker, an amine linker, and a sulfonamide linker.

An amide linker is formed via an amide bond between an amine on one component such as the antigen or adjuvant with the carboxylic acid group of a second component such as the nanocarrier. The amide bond in the linker can be made using any of the conventional amide bond forming reactions with suitably protected amino acids or antigens or adjuvants and activated carboxylic acid such N-hydroxysuccinimide-activated ester.

A disulfide linker is made via the formation of a disulfide (S—S) bond between two sulfur atoms of the form, for instance, of R1-S—S-R2. A disulfide bond can be formed by thiol exchange of an antigen or adjuvant containing thiol/mercaptan group (—SH) with another activated thiol group on a polymer or nanocarrier or a nanocarrier containing thiol/mercaptan groups with a antigen or adjuvant containing activated thiol group.

A triazole linker, specifically a 1,2,3-triazole of the form

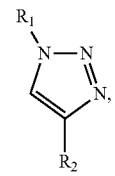

wherein R1 and R2 may be any chemical entities, is made by the 1,3-dipolar cycloaddition reaction of an azide attached to a first component such as the nanocarrier with a terminal alkyne attached to a second component such as the peptide. The 1,3-dipolar cycloaddition reaction is performed with or without a catalyst, preferably with Cu(I)-catalyst, which links the two components through a 1,2,3-triazole function. This chemistry is described in detail by Sharpless et al., Angew. Chem. Int. Ed. 41(14), 2596, (2002) and Meldal, et al, Chem. Rev., 2008, 108(8), 2952-3015 and is often referred to as a "click" reaction or CuAAC.

In embodiments, a polymer containing an azide or alkyne group, terminal to the polymer chain is prepared. This polymer is then used to prepare a synthetic nanocarrier in such a manner that a plurality of the alkyne or azide groups are positioned on the surface of that nanocarrier. Alternatively, the synthetic nanocarrier can be prepared by another route, and subsequently functionalized with alkyne or azide groups. The antigen or adjuvant is prepared with the presence of either an alkyne (if the polymer contains an azide) or an azide (if the polymer contains an alkyne) group. The antigen or adjuvant is then allowed to react with the nanocarrier via the 1,3-dipolar cycloaddition reaction with or without a catalyst which covalently couples the antigen or adjuvant to the particle through the 1,4-disubstituted 1,2,3-triazole linker.

A thioether linker is made by the formation of a sulfur-carbon (thioether) bond in the form, for instance, of R1-S-R2. Thioether can be made by either alkylation of a thiol/mercaptan (—SH) group on one component such as the antigen or adjuvant with an alkylating group such as halide or epoxide on a second component such as the nanocarrier. Thioether linkers can also be formed by Michael addition of a thiol/mercaptan group on one component such as a antigen or adjuvant to an electron-deficient alkene group on a second component such as a polymer containing a maleimide group or vinyl sulfone group as the Michael acceptor. In another way, thioether linkers can be prepared by the radical thiol-ene reaction of a thiol/mercaptan group on one component such as a antigen or adjuvant with an alkene group on a second component such as a polymer or nanocarrier.

A hydrazone linker is made by the reaction of a hydrazide group on one component such as the antigen or adjuvant with an aldehyde/ketone chemistry group on the second component such as the nanocarrier.

A hydrazide linker is formed by the reaction of a hydrazine group on one component such as the antigen or adjuvant with a carboxylic acid group on the second component such as the nanocarrier. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one component such as the antigen or adjuvant with an aldehyde or ketone group on the second component such as the nanocarrier.

An urea or thiourea linker is prepared by the reaction of an amine group on one component such as the antigen or adjuvant with an isocyanate or thioisocyanate group on the second component such as the nanocarrier.

An amidine linker is prepared by the reaction of an amine group on one component such as the antigen or adjuvant with an imidoester group on the second component such as the nanocarrier.

An amine linker is made by the alkylation reaction of an amine group on one component such as the antigen or adjuvant with an alkylating group such as halide, epoxide, or sulfonate ester group on the second component such as the nanocarrier. Alternatively, an amine linker can also be made by reductive amination of an amine group on one component such as the antigen or adjuvant with an aldehyde or ketone group on the second component such as the nanocarrier with a suitable reducing reagent such as sodium cyanoborohydride or sodium triacetoxyborohydride.

A sulfonamide linker is made by the reaction of an amine group on one component such as the antigen or adjuvant with a sulfonyl halide (such as sulfonyl chloride) group on the second component such as the nanocarrier.

A sulfone linker is made by Michael addition of a nucleophile to a vinyl sulfone. Either the vinyl sulfone or the nucleophile may be on the surface of the nanoparticle or attached to the antigen or adjuvant.

The antigen or adjuvant can also be conjugated to the nanocarrier via non-covalent conjugation methods. For examples, a negative charged antigen or adjuvant can be conjugated to a positive charged nanocarrier through electrostatic adsorption. An antigen or adjuvant containing a metal ligand can also be conjugated to a nanocarrier containing a metal complex via a metal-ligand complex.

In embodiments, the antigen or adjuvant can be attached to a polymer, for example polylactic acid-block-polyethylene glycol, prior to the assembly of the synthetic nanocarrier or the synthetic nanocarrier can be formed with reactive or activatible groups on its surface. In the latter case, the antigen or adjuvant is prepared with a group which is compatible with the attachment chemistry that is presented by the synthetic nanocarriers' surface. In other embodiments, agents, such as a peptide antigen, can be attached to VLPs or liposomes using a suitable linker. A linker is a compound or reagent that capable of coupling two molecules together. In an embodiment, the linker can be a homobifunctional or heterobifunctional reagent as described in Hermanson 2008. For example, an VLP or liposome synthetic nanocarrier containing a carboxylic group on the surface can be treated with a homobifunctional linker, adipic dihydrazide (ADH), in the presence of EDC to form the corresponding synthetic nanocarrier with the ADH linker. The resulting ADH linked synthetic nanocarrier is then conjugated with an agent containing an acid group via the other end of the ADH linker on the NC to produce the corresponding VLP or liposome peptide conjugate.

For detailed descriptions of available conjugation methods, see Hermanson G T "Bioconjugate Techniques", 2nd Edition Published by Academic Press, Inc., 2008. In addition to covalent attachment the antigen or adjuvant can be coupled by adsorbtion to a pre-formed synthetic nanocarrier or it can be coupled by encapsulation during the formation of the synthetic nanocarrier.

Methods of Making and Using the Inventive Methods and Related Compositions

Synthetic nanocarriers may be prepared using a wide variety of methods known in the art. For example, synthetic nanocarriers can be formed by methods as nanoprecipitation, flow focusing using fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755, U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

Various materials may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6): 843-853 (2010). Other methods suitable for encapsulating materials, such as oligonucleotides, into synthetic nanocarriers may be used, including without limitation methods disclosed in U.S. Pat. No. 6,632,671 to Unger Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be coupled to the synthetic nanocarriers and/or the composition of the polymer matrix.

If particles prepared by any of the above methods have a size range outside of the desired range, particles can be sized, for example, using a sieve.

Elements of the inventive synthetic nanocarriers—such as targeting moieties, polymeric matrices, antigens, adjuvants and the like—may be coupled to the synthetic nanocarrier, e.g., by one or more covalent bonds, or may be coupled by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Alternatively or additionally, synthetic nanocarriers can be coupled to an element, such as immunofeature surfaces, targeting moieties, adjuvants, various antigens, etc. directly or indirectly via non-covalent interactions. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Such couplings may be arranged to be on an external surface or an internal surface of an inventive synthetic nanocarrier. In embodiments, encapsulation and/or absorption is a form of coupling.

In embodiments, the inventive synthetic nanocarriers can be combined with other adjuvants by admixing in the same vehicle or delivery system. Such adjuvants may include, but are not limited to mineral salts, such as alum, alum combined with monphosphoryl lipid (MPL) A of Enterobacteria, such as *Escherichia coli, Salmonella minnesota, Salmonella typhimurium*, or *Shigella flexneri* or specifically with MPL® (AS04), AS15, MPL A of above-mentioned bacteria separately, saponins, such as QS-21, Quil-A, ISCOMs, ISCOMATRIX™, emulsions such as MF59™, Montanide® ISA 51 and ISA 720, AS02 (QS21+squalene+MPL®), liposomes and liposomal formulations such as AS01, synthesized or specifically prepared microparticles and microcarriers such as bacteria-derived outer membrane vesicles (OMV) of *N. gonorrheae, Chlamydia trachomatis* and others, or chitosan particles, depot-forming agents, such as Pluronic® block copolymers, specifically modified or prepared peptides, such as muramyl dipeptide, aminoalkyl glucosaminide 4-phosphates, such as RC529, or proteins, such as bacterial toxoids or toxin fragments. Additional useful adjuvants may be found in WO 2002/032450; U.S. Pat. No. 7,357,936 "Adjuvant Systems and Vaccines"; U.S. Pat. No. 7,147,862 "Vaccine composition containing adjuvants"; U.S. Pat. No. 6,544,518 "Vaccines"; U.S. Pat. No. 5,750,110 "Vaccine composition containing adjuvants." The doses of such other adjuvants can be determined using conventional dose ranging studies. In embodiments, adjuvant that is not coupled to the recited synthetic nanocarriers, if any, may be the same or different from adjuvant that is coupled to the synthetic nanocarriers In embodiments, any adjuvant coupled to the inventive synthetic nanocarriers can be different, similar or identical to those not coupled to a nanocarrier (with or without antigen, utilizing or not utilizing another delivery vehicle). The adjuvants (coupled and not coupled) can be administered separately at a different time-point and/or at a different body location and/or by a different immunization route or with another adjuvant-carrying synthetic nanocarrier (with or without antigen) administered separately at a different time-point and/or at a different body location and/or by a different immunization route.

Populations of synthetic nanocarriers may be combined to form pharmaceutical dosage forms according to the present invention using traditional pharmaceutical mixing methods. These include liquid-liquid mixing in which two or more suspensions, each containing one or more subset of nanocarriers, are directly combined or are brought together via one or more vessels containing diluent. As synthetic nanocarriers may also be produced or stored in a powder form, dry powder-powder mixing could be performed as could the re-suspension of two or more powders in a common media. Depending on the properties of the nanocarriers and their interaction potentials, there may be advantages conferred to one or another route of mixing.

Typical inventive compositions that can be used in the inventive methods comprise synthetic nanocarriers may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions that can be used in the methods according to the invention comprise inventive synthetic nanocarriers in combination with pharmaceutically acceptable excipients. The compositions may be made using conventional pharmaceutical manufacturing and compounding techniques to arrive at useful dosage forms. Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, inventive synthetic nanocarriers are suspended in sterile saline solution for injection together with a preservative.

It is to be understood that the compositions that can be used in the methods of the invention can be made in any suitable manner, and the invention is in no way limited to the use of compositions that can be produced using the methods described herein. Selection of an appropriate method may require attention to the properties of the particular moieties being associated.

In some embodiments, inventive synthetic nanocarriers are manufactured under sterile conditions or are terminally sterilized. This can ensure that resulting composition are sterile and non-infectious, thus improving safety when compared to non-sterile compositions. This provides a valuable safety measure, especially when subjects receiving synthetic nanocarriers have immune defects, are suffering from infection, and/or are susceptible to infection. In some embodiments, inventive synthetic nanocarriers may be lyophilized and stored in suspension or as lyophilized powder depending on the formulation strategy for extended periods without losing activity.

The compositions that can be used in the inventive methods may be administered by a variety of routes of administration, including but not limited to subcutaneous, intramuscular, intradermal, oral, intranasal, transmucosal, sublingual, rectal, ophthalmic, transdermal, transcutaneous or by a combination of these routes.

Doses of dosage forms contain varying amounts of populations of synthetic nanocarriers and/or varying amounts of adjuvants and/or antigens, according to the invention. The amount of synthetic nanocarriers and/or adjuvants and/or antigens present in the inventive dosage forms can be varied according to the nature of the adjuvants and/or antigens, the therapeutic benefit to be accomplished, and other such parameters. In some embodiments, the doses of the dosage forms are sub-therapeutic or toxicity-reduced doses. In other embodiments, the doses are amounts effective to generate one or more immune responses as provided herein. In some embodiments, the immune response(s) is an antibody response or generation of an antibody titer and/or systemic cytokine release. In embodiments, dose ranging studies can be conducted to establish optimal therapeutic amount of the population of synthetic nanocarriers and/or the amount of adjuvants and/or antigens to be present in the dosage form. In embodiments, the synthetic nanocarriers and/or the adjuvants and/or antigens are present in the dosage form in an amount effective to generate an immune response as provided herein upon administration to a subject. In some embodiments, the subject is a human. It may be possible to determine amounts of the adjuvants and/or antigens effective to generate an immune response as provided herein using conventional dose ranging studies and techniques in subjects. Inventive dosage forms may be administered at a variety of frequencies. In a preferred embodiment, at least one administration of the dosage form is sufficient to generate a pharmacologically relevant response. In more preferred embodiment, at least two administrations, at least three administrations, or at least four administrations, of the dosage form are utilized to ensure a pharmacologically relevant response.

The compositions and methods described herein can be used to induce, enhance, stimulate, modulate, direct or redirect an immune response. The compositions and methods described herein can be used in the diagnosis, prophylaxis and/or treatment of conditions such as cancers, infectious diseases, metabolic diseases, degenerative diseases, autoimmune diseases, inflammatory diseases, immunological diseases, or other disorders and/or conditions. The compositions and methods described herein can also be used for the prophylaxis or treatment of an addiction, such as an addiction to nicotine or a narcotic. The compositions and methods described herein can also be used for the prophylaxis and/or treatment of a condition resulting from the exposure to a toxin, hazardous substance, environmental toxin, or other harmful agent.

In embodiments, the compositions and methods provided can be used to systemically induce cytokines, such as TNF-α, IL-6 and/or IL-12, or IFN-γ, IL-12 and/or IL-18. In other embodiments, the compositions and methods provided can be used to induce an antibody response or to generate an antibody titer. The immune responses as provided herein can be specific to an antigen, such as any of the antigens provided herein, preferably to one or more antigens in an inventive composition or that is administered according to an inventive method provided herein.

The compositions and methods provided herein can be used in a variety of subjects. The subjects provided herein can have or be at risk of having cancer. Cancers include, but are not limited to, breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia, e.g., B Cell CLL; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor.

The subjects provided herein can have or be at risk of having an infection or infectious disease. Infections or infectious diseases include, but are not limited to, viral infectious diseases, such as AIDS, Chickenpox (Varicella), Common cold, Cytomegalovirus Infection, Colorado tick fever, Dengue fever, Ebola hemorrhagic fever, Hand, foot and mouth disease, Hepatitis, Herpes simplex, Herpes zoster, HPV, Influenza (Flu), Lassa fever, Measles, Marburg hemorrhagic fever, Infectious mononucleosis, Mumps, Norovirus, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease and Yellow fever; bacterial infectious diseases, such as Anthrax, Bacterial Meningitis, Botulism, Brucellosis, Campylobacteriosis, Cat Scratch Disease, Cholera, Diphtheria, Epidemic Typhus, Gonorrhea, Impetigo, Legionellosis, Leprosy (Hansen's Disease), Leptospirosis, Listeriosis, Lyme disease, Melioidosis, Rheumatic Fever, MRSA infection, Nocardiosis, Pertussis (Whooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus and Urinary Tract Infections; parasitic infectious diseases, such as African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trichomoniasis and Trypanosomiasis; fungal infectious disease, such as Aspergillosis, Blastomycosis, Candidiasis, Coccidioidomycosis, Cryptococcosis, Histoplasmosis, Tinea pedis (Athlete's Foot) and Tinea cruris; prion infectious diseases, such as Alpers' disease, Fatal Familial Insomnia, Gerstmann-Sträussler-Scheinker syndrome, Kuru and Variant Creutzfeldt-Jakob disease.

Subjects provided here also include those that have or are at risk of having an atopic condition, such as but not limited to allergy, allergic asthma, or atopic dermatitis; asthma; chronic obstructive pulmonary disease (COPD, e.g. emphysema or chronic bronchitis); and chronic infections due to chronic infectious agents such as chronic Leishmaniasis, candidiasis or schistosomiasis and infections caused by plasmodia, toxoplasma gondii, mycobacteria, HIV, HBV, HCV EBV or CMV, or any one of the above, or any subset of the above.

EXAMPLES

Example 1

Synthetic Nanocarriers with Covalently Coupled Adjuvant (Prophetic)

Resiquimod (aka R848) is synthesized according to the synthesis provided in Example 99 of U.S. Pat. No. 5,389,640 to Gerster et al. PLA-R848 conjugate is prepared. PLA-PEG-nicotine conjugate is prepared. PLA is prepared by a ring opening polymerization using D,L-lactide (MW=approximately 15 KD-18 KD). The PLA structure is confirmed by NMR. The polyvinyl alcohol (Mw=11 KD-31 KD, 85% hydrolyzed) is purchased from VWR scientific.

These are used to prepare the following solutions:
1. PLA-R848 conjugate @100 mg/mL in methylene chloride
2. PLA-PEG-nicotine in methylene chloride @100 mg/mL
3. PLA in methylene chloride @100 mg/mL
4. Polyvinyl alcohol in water @50 mg/mL.

Solution #1 (0.25 to 0.75 mL), solution #2 (0.25 mL) and solution #3 (0.25 to 0.5 mL) are combined in a small vial with distilled water (0.5 mL), and the mixture is sonicated at 50% amplitude for 40 seconds using a Branson Digital Sonifier 250. To this emulsion is added solution #4 (2.0 mL) and sonication at 35% amplitude for 40 seconds using the Branson Digital Sonifier 250 forms the second emulsion. This is added to a beaker containing phosphate buffer solution (30 mL), and this mixture is stirred at room temperature for 2 hours to form the nanocarriers. To wash the nanocarriers, a portion of the nanocarrier dispersion (7.0 mL) is transferred to a centrifuge tube and spun at 5,300 g for one hour, supernatant is removed, and the pellet is re-suspended in 7.0 mL of phosphate buffered saline. The centrifuge procedure is repeated and the pellet is re-suspended in 2.2 mL of phosphate buffered saline for a final nanocarrier dispersion of about 10 mg/mL.

Example 2

Synthetic Nanocarriers with Non-Covalently Coupled Adjuvant (Prophetic)

Charged nanocarriers are made as follows:
1. PLA-PEG-OMe in methylene chloride @100 mg/mL
2. PLA in methylene chloride @100 mg/mL
3. Cetyl trimethylammonium bromide (CTAB) in water at 5 mg/mL Solution #1 (0.25 to 0.75 mL), solution #2 (0.25 mL) and distilled water (0.5 mL) are combined in a small vial and the mixture is sonicated at 50% amplitude for 40 seconds using a Branson Digital Sonifier 250. To this emulsion is added solution #3 (2.0 mL) and sonication at 35% amplitude for 40 seconds using the Branson Digital Sonifier 250 forms the second emulsion. This is added to a beaker containing phosphate buffer solution (30 mL), and this mixture is stirred at room temperature for 2 hours to form the nanocarriers. To wash the nanocarriers a portion of the nanocarrier dispersion (7.0 mL) is transferred to a centrifuge tube and spun at 5,300 g for one hour, supernatant is removed, and the pellet is re-suspended in 7.0 mL of phosphate buffered saline. The centrifuge procedure is repeated and the pellet is re-suspended in 2.2 mL of DI water for a final nanocarrier dispersion of about 10 mg/mL. To adsorb an antigen, in this case CpG DNA, to the nanocarriers, 1.0 mL of the charged nanocarriers in DI water at 10 mg/mL are cooled on ice. To this cooled suspension is added 10 µg of CpG DNA ODN 1826, and this mixture is incubated at 4° C. for 4 hours. The nanocarriers are then isolated and washed as described above.

Example 3

Composition with Synthetic Nanocarriers and Uncoupled Antigen (Prophetic)

The polyvinyl alcohol (Mw=11 KD-31 KD, 87-89% partially hydrolyzed) is purchased from JT Baker. Ovalbumin peptide 323-339 is obtained from Bachem Americas Inc. (3132 Kashiwa Street, Torrance Calif. 90505. Part #4065609). PLGA-R848 (or PLA-R848) and PLA-PEG-Antigen or PLA-PEG-Linker or PLA-PEG-OMe conjugates are synthesized and purified.

The above materials are used to prepare the following solutions:
1. PLA-R848 or PLGA-R848 conjugate in methylene chloride @100 mg/mL
2. PLA-PEG-OMe in methylene chloride @100 mg/mL
3. PLA or PLGA in methylene chloride @100 mg/mL
4. Polyvinyl alcohol in 100 mM pH 8 phosphate buffer @50 mg/mL Solution #1 (0.1 to 0.9 mL) and solution #2 (0.01 to 0.50 mL) are combined, optionally also including solution #3 (0.1 to 0.89 mL), and then distilled water (0.50 mL) is added in a small vessel and the mixture is sonicated at 50% amplitude for 40 seconds using a Branson Digital Sonifier 250. To this emulsion is added solution #4 (2.0-3.0 mL) and sonication at 30% amplitude for 40 seconds using the Branson Digital Sonifier 250 forms the second emulsion. This is added to a stirring beaker containing a 70 mM pH 8 phosphate buffer solution (30 mL), and this mixture is stirred at room temperature for 2 hours to form the nanocarriers. To wash the nanocarriers, a portion of the nanocarrier dispersion (25 to 32 mL) is transferred to a 50 mL centrifuge tube and spun at 9500 rpm (13,800 g) for one hour at 4° C., supernatant is removed, and the pellet is re-suspended in 25 to 32 mL of phosphate buffered saline. The centrifugation procedure is repeated and the pellet is re-suspended in phosphate buffered saline to achieve a final nominal nanocarrier concentration of 10 mg/mL.

The nanocarriers are combined with the necessary amount of sterile saline solution to reach the final concentration in a sterile vehicle, and then administered to a subject by subcutaneous or intramuscular injection using a conventional slip-tip or Luer-lock syringe.

Example 4

Administration of Synthetic Nanocarriers and Non-Coadministered Antigen (Prophetic)

The synthetic nanocarriers of Example 3 are formulated into a sterile saline vehicle, and then administered to a subject by subcutaneous or intramuscular injection using a conventional slip-tip or Luer-lock syringe. The subject is exposed to environmental antigen (e.g. pollen, animal antigens, etc.) that is not coadministered with the synthetic nanocarriers. Any altered immune response to the non-coadministered antigen that is due to the administration of the synthetic nanocarriers is noted.

Example 5

Synthetic Nanocarriers with Covalently Coupled Adjuvant

Virus-like particles (VLP's) have received attention as nanocarriers for use in vaccines and for drug delivery. These virus-like particles can also be used to deliver covalently attached adjuvants. Virus-like particles can be made by a variety of methods, for example, as described in Biotechnology and Bioengineering 100(1), 28, (2008). Covalent attachment can be accomplished as follows.

A suspension of virus-like particles in PBS (1.0 mL, 300 µg/mL) is cooled on ice. To this is added the R-848 conjugate (50 mg, described below) in PBS (0.5 mL). EDC hydrochloride (50 mg) is added and the mixture is gently stirred overnight at ice temperature. The resulting VLP conjugate is freed from excess R848 conjugate by dialysis.

The R848 conjugate is made as follows. R848 (5.0 gm, $1.59 \times 10^{-2}$ moles) and diglycolic anhydride (3.7 gm, $3.18 \times 10^{-2}$ moles) are combined in dimethylacetamide (10 mL). This solution is heated at 120° C. for 2 hours. After cooling slightly, 2-propanol (25 mL) is added, and the resulting solution is stirred on ice for 1 hour. The imide separates as a white solid which is isolated by filtration, washed with 2-propanol and dried. The yield of the R848 imide is 6.45 gm (98%).

The R848 imide (412 mg, $1.0 \times 10^{-3}$ moles) and 6-hydroxycaproic acid (132 mg, $1.0 \times 10^{-3}$ moles) are stirred in methylene chloride (5 mL). To this suspension is added 1,5,7-triazabicyclo[4,4,0]dec-5-ene (TBD, 278 mg, $2 \times 10^{-3}$ moles) after which the suspension is stirred overnight at room temperature. The resulting clear solution is diluted with methylene chloride (25 mL), and this solution is washed with 5% citric acid solution (2×25 mL). After drying over magnesium sulfate the solution is filtered and evaporated under vacuum to provide the R848 conjugate used in the VLP-antigen synthesis. The expected R848 conjugate structure is as follows:

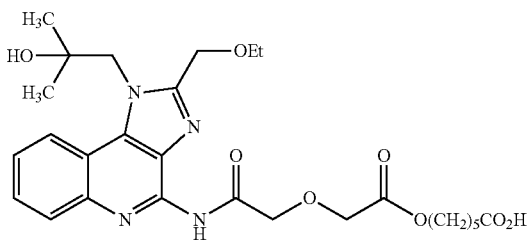

Example 6

Figure 1B:
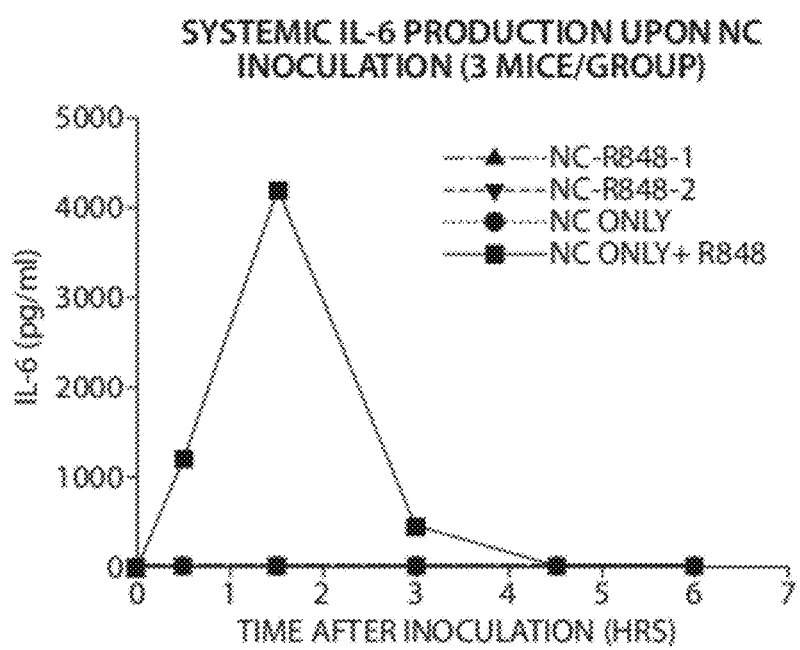
Figure 1C:
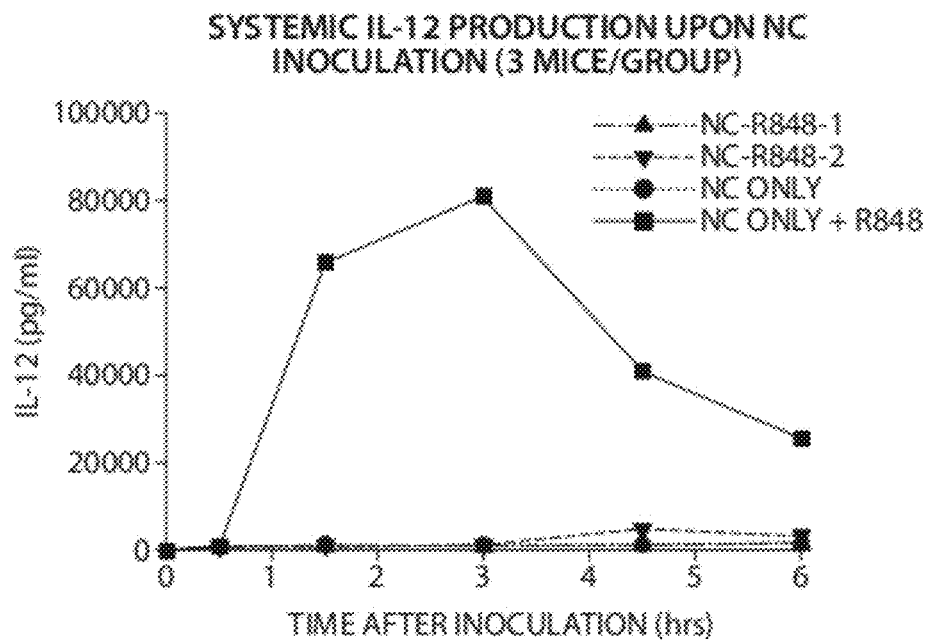

Coupling of Nanocarrier to R848 Adjuvant Abolishes Systemic Production of Inflammatory Cytokines Groups of mice were injected subcutaneously into hind limbs with 100 µg of nanocarriers (NC) coupled, non-coupled or admixed with small molecule nucleoside analogue and known TLR7/8 agonist and adjuvant R848. R848 amount in nanocarrier was 2-3% resulting in 2-3 µg of coupled R848 per injection; amount of free R848 used was 20 µg per injection. Mouse serum was taken by terminal bleed and systemic cytokine production in serum was measured at different timepoints by ELISA (BD Biosciences). As seen in FIGS. 1A-1C, strong systemic production of major pro-inflammatory cytokines TNF-α, IL-6 and IL-12 was observed when admixed R848 (NC+R848) was used, while no expression of TNF-α, IL-6 and IL-12 was detected when two separate preparations of NC coupled with R848 (NC-R848-1 and NC-R848-2) were used. The difference in peak cytokine expression levels was >100-fold for TNF-α and IL-6, and >50-fold for IL-12. NC not coupled to R848 (labeled as NC only) did not induce any systemic cytokines when used without admixed R848.

Example 7

Coupling of Nanocarrier to R848 Adjuvant does not Inhibit Systemic Production of Immune Cytokine IFN-γ

Figure 2:
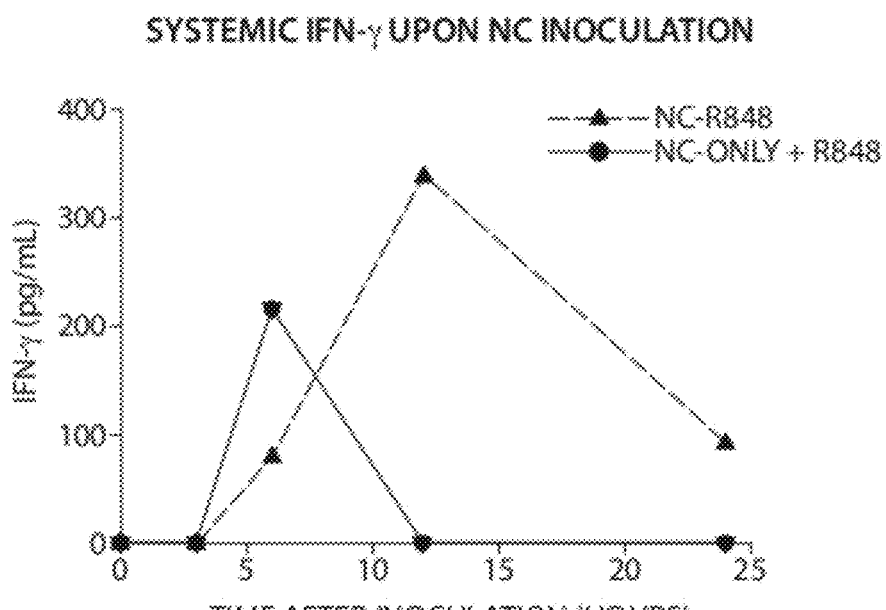
FIG. 2 shows the systemic IFN-γ production in mice after NC inoculation. Sera from groups of three mice were pooled and analyzed by ELISA.

While early proinflammatory cytokines are associated with side effects during immunization, the production of other cytokines, such as immune IFN-γ is known to be important for induction of effective immune response. Therefore, an experiment was performed identically to that of Example 6. Systemic production of immune cytokine IFN-γ (as measured in mouse serum by ELISA, BD Biosciences), which is instrumental for Th1 immune response, was seen to reach the same level irrespectively of whether NC-R848 (containing 2 µg of R848) or NC with admixed R848 (20 µg) was used (FIG. 2). Furthermore, the production of IFN-γ by NP-R848 was distributed over a wider time window.

Example 8

Figure 3:
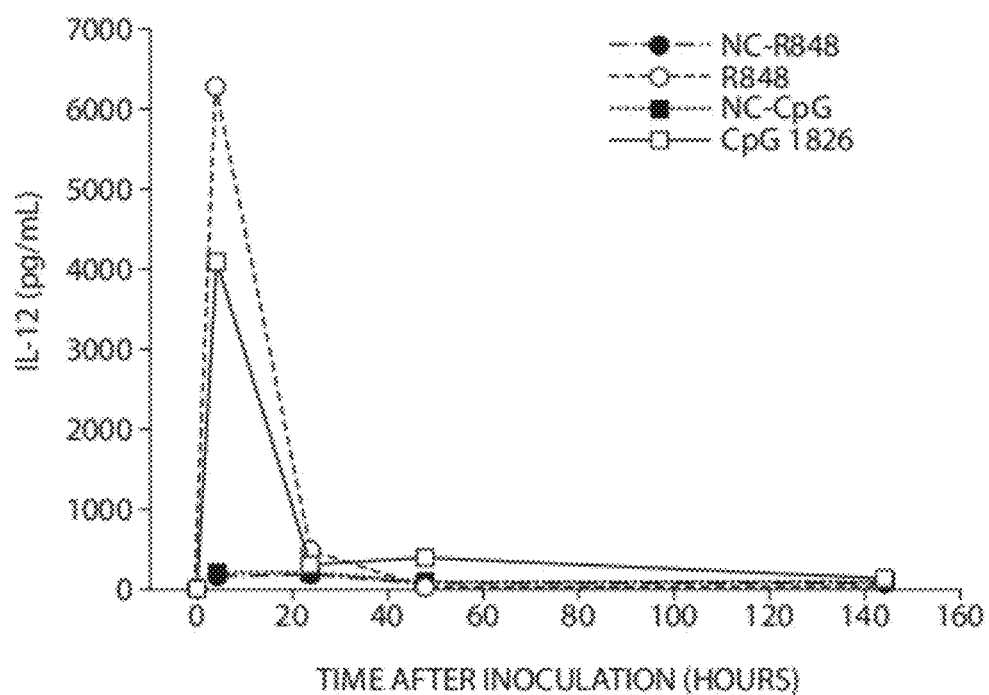
FIG. 3 shows the systemic IL-12 production in mice after inoculation with free or NC-coupled TLR agonists. Sera from groups of two mice were pooled and analyzed by ELISA.

The Production of Systemic IL-12 by Adjuvants R848 and CpG is Abolished by their Coupling to Nanocarriers The effect on systemic cytokine induction by coupling of a TLR agonist to a nanocarrier was demonstrated to not be specific to a particular TLR agonist. In this experiment groups of two mice were inoculated by free TLR agonists R848 or CpG 1826 (20 µg each) and by the same molecules coupled to nanocarriers, NC-R848 (100 µg of NC prep, containing a total of 3 µg of R848) or NC-CpG (100 µg of NC prep, containing a total of 5 µg of CpG 1826), and serum IL-12 measured at times indicated in pooled mouse sera (ELISA, BD Biosciences). As seen in FIG. 3, peak levels of systemic IL-12 were 30-fold higher by free R848 than by NC-R848 and 20-fold higher by free CpG 1826 than by NC-CpG).

Example 9

Figure 4:
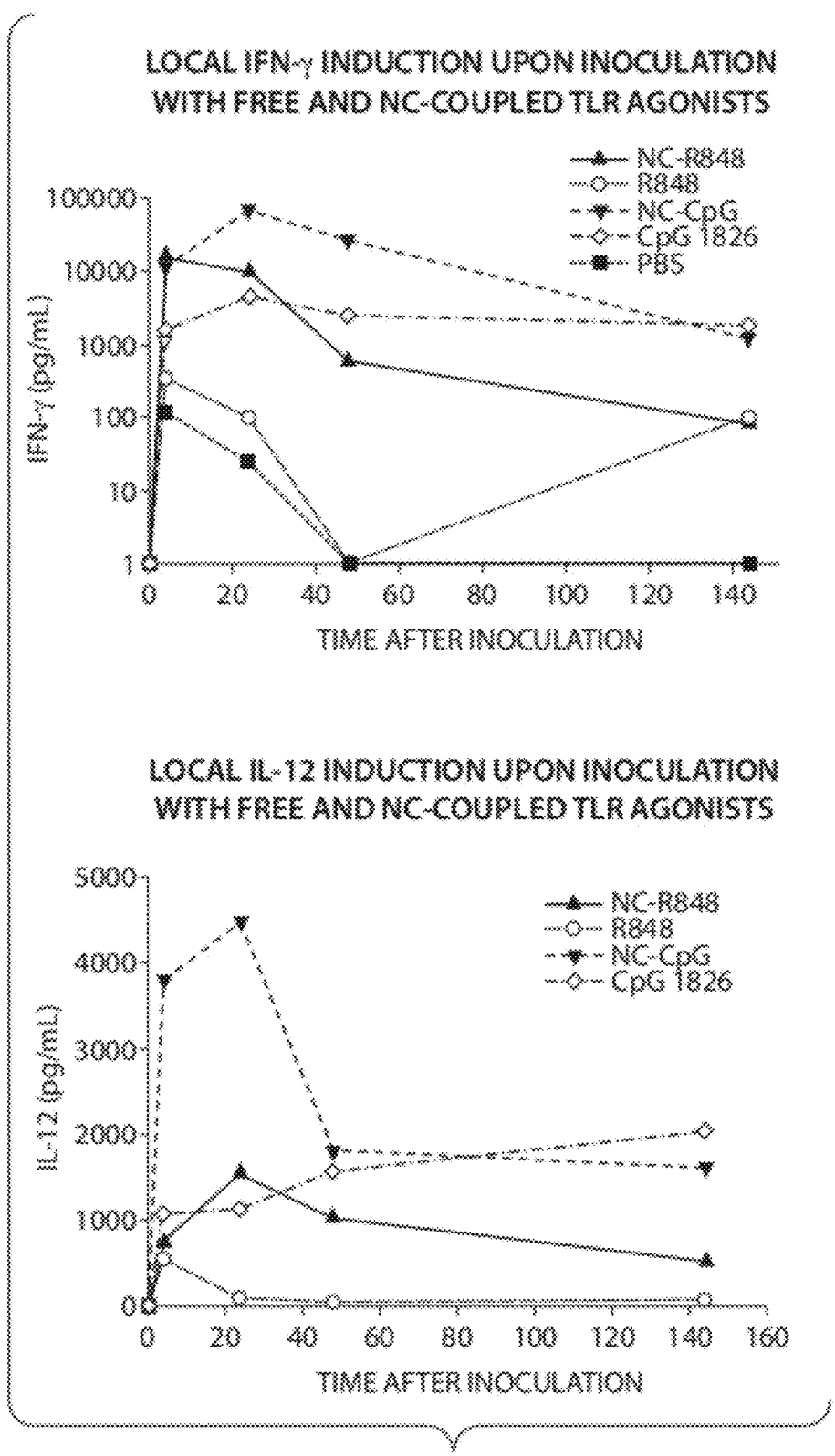
FIG. 4 shows the local induction of immune cytokines by free or NC-coupled TLR agoinsts. Each point represents an average of two lymph nodes (LNs) from separate mice.
Figure 4:
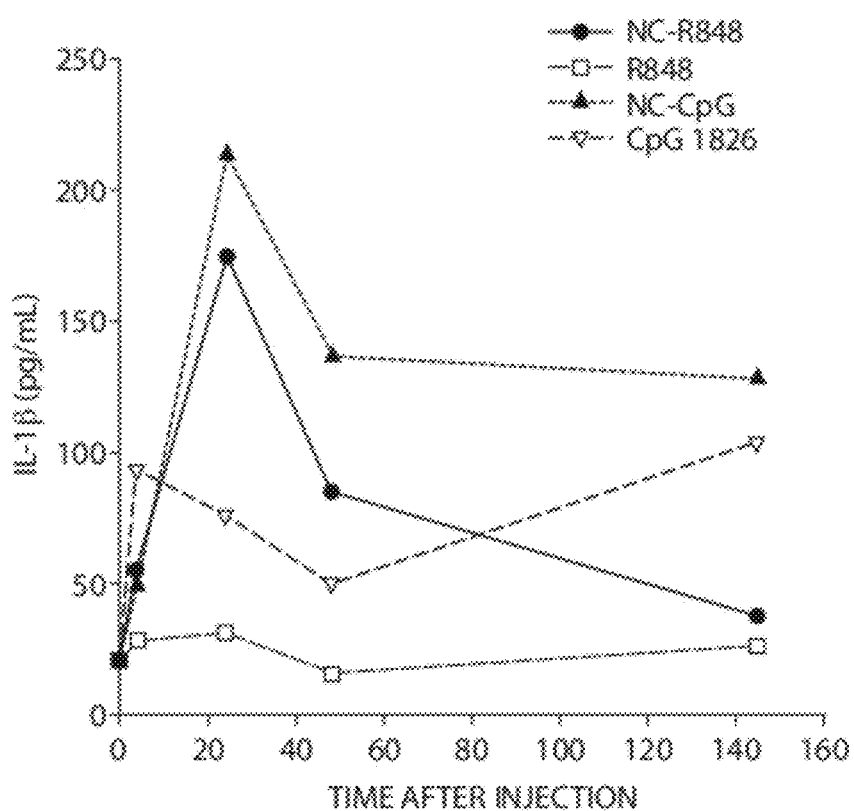

Local Induction of Immune Cytokines IFN-γ, IL-12 and IL-1β is Strongly Augmented by Adjuvant Coupling to Nanocarriers, while Adjuvant is Spared While systemic induction of pro-inflammatory cytokines is associated with adverse effects of vaccination, local induction of immune cytokines, such as IFN-γ or IL-1β, is viewed as mostly beneficial for the induction of specific and localized immune response. In the experiment shown in FIG. 4, mice were injected subcutaneously at the hind limb by free (20 µg) or NC-coupled R848 and CpG adjuvants (adjuvant content 2.5-4 µg), draining (popliteal) lymph nodes (LN) removed at times indicated, incubated overnight in a standard cell culture medium and cytokine production in cell supernatants measured by ELISA as described above. Much stronger local induction of Th1 cytokines IFN-γ (50-100-fold, FIG. 4A) and IL-12 (17-fold, FIG. 4B) and inflammasome-related cytokine IL-1β (6-fold, FIG. 4C) was observed when NC-R848 was used compared to free R848 (notably, the amounts of R848 present in NC-R848 were 5-10 times less than of free R848). Similarly, NC-CpG was a much stronger inducer of local immune cytokines than free CpG (known to be extremely potent in this regard). Local production of IFN-γ was 7-15 times higher at peak levels (FIG. 4A), production of IL-12 was 4 times higher (FIG. 4B), and production of IL-1β was 2 times higher (FIG. 4C). The amount of CpG 1826 present in NC-CpG was 4-5 times less than of free CpG 1826.

Example 10

Local Lymph Node (LN) Stimulation and Induction of Immune Cell Proliferation by NC-Coupled R848 Adjuvant, but not by Free R848

Figure 5:
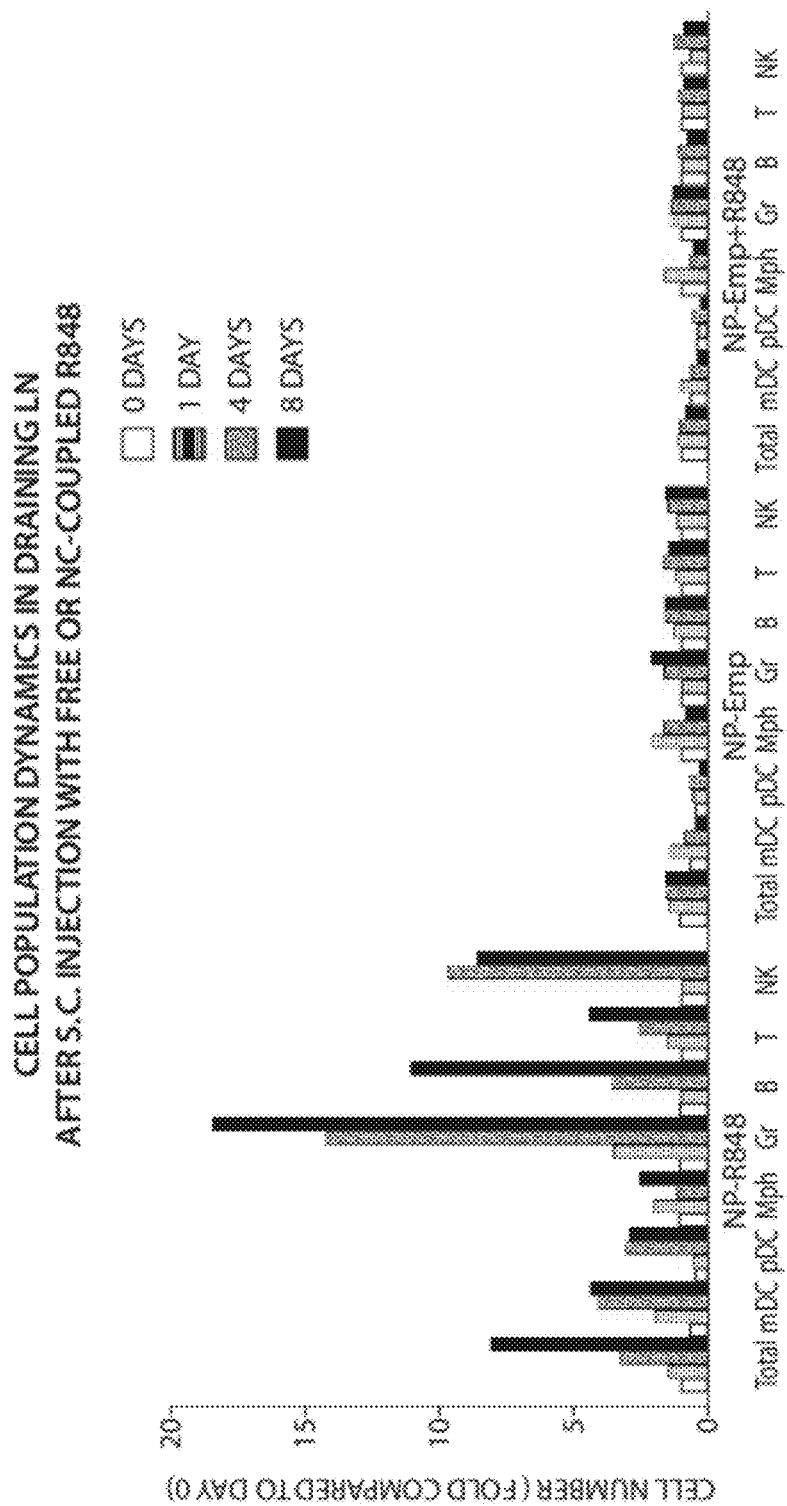
FIG. 5 shows the cell population dynamics in popliteal lymph nodes after inoculation with free and NC-coupled TLR7/8 agonist R848. Three intact mice were sacrificed at different days and the average cell counts from their popliteal LN assigned "day 0" meaning of "1" to which all other numbers were compared. Each bar from R848- or NC-inoculated group represents an average from two lymph nodes taken from independent animals.

Draining lymph node swelling (lymphadenopathy) is a hallmark of local immune activation. It results from infiltration of LN infiltration by different cells instrumental for innate and adaptive immune response. Mice were subcutaneously inoculated with NC-R848, NC only or with NC-R848 in hind limbs as described above. Popliteal LNs were removed at times indicated (FIG. 5), and the number of total cells as well as separate immune cell population counted. Hemocytometer was used for total cell counts, and then cell populations were differentially stained by surface cell markers and percentage of positive for each population determined using FACS. DC: dendritic cells, mDC: myeloid DC, pDC: plasmacytoid DC, Mph: macrophages, Gr: granulocytes, B: B cells, T: T cells, NK: natural killer cells. The following markers were used for staining: $CD11c^+$ (DC); $CD11c^+B220^-$ (mDC); $CD11c^+B220^+$ (pDC); $F4/80+/Gr1^-$ (Mph); $F4/80^-/Gr1^+$ (Gr); $B220^+CD11c^-$ (B cells); $CD3^+$ (T cells); $CD3^-/CD49b^+$ (NK cells). Major increase in total cell number in draining LN was seen after injection with NC-R848 with DC, granulocytes, B-cells and NK cells showing the most pronounced effect (FIG. 5).

Example 11

Antibody Response Higher for Nanocarrier with Conjugated Adjuvant Versus Admixed Adjuvant Materials for Nic,R848,OP-II Nanocarrier Formulations Ovalbumin peptide 323-339 amide TFA salt, was purchased from Bachem Americas Inc. (3132 Kashiwa Street, Torrance Calif. 90505. Part #4064565.) PLA with an inherent viscosity of 0.19 dL/g was purchased from Boehringer Ingelheim (Ingelheim Germany. Product Code R202H). PLA-R848 conjugate having molecular weight of approximately 2500 Da and R848 content of approximately 13.6% by weight was synthesized by a ring-opening process. PLA-PEG-Nicotine with a nicotine-terminated PEG block of approximately 3,500 Da and DL-PLA block of approximately 15,000 Da was synthesized. Polyvinyl alcohol (Mw=11,000-31,000, 87-89% hydrolyzed) was purchased from J.T. Baker (Part Number U232-08).

Methods for Nic,R848,OP-II Nanocarrier Production

Solutions were prepared as follows:

Solution 1: Ovalbumin peptide 323-339 @69 mg/mL was prepared in distilled water at room temperature.

Solution 2: PLA-R848 @50 mg/mL, PLA @25 mg/mL, and PLA-PEG-Nicotine @25 mg/mL in dichloromethane was prepared by dissolving the polymers at 100 mg/mL, combining the PLA-R848 and PLA solutions at a 2:1 ratio, and then adding 1 part PLA-PEG-Nicotine solution to 3 parts of the PLA-R848/PLA solution.

Solution 3: Polyvinyl alcohol @50 mg/mL in 100 mM in deionized water.

Solution 4: 70 mM phosphate buffer, pH 8.

A primary (W1/O) emulsion was first created using Solution 1 and Solution 2. Solution 1 (0.1 mL) and Solution 2 (1.0 mL) were combined in a small glass pressure tube and sonicated at 50% amplitude for 40 seconds using a Branson Digital Sonifier 250. A secondary (W1/O/W2) emulsion was then formed by adding Solution 3 (2.0 mL) to the primary emulsion and sonicating at 35% amplitude for 40 seconds using the Branson Digital Sonifier 250. The secondary emulsion was added to a beaker containing 70 mM phosphate buffer solution (30 mL) in an open 50 ml beaker and stirred at room temperature for 2 hours to allow for the dichloromethane to evaporate and for the nanocarriers to form in suspension. A portion of the suspended nanocarriers were washed by transferring the nanocarrier suspension to a centrifuge tube, spinning at 5,300 rcf for 60 minutes, removing the supernatant, and re-suspending the pellet in phosphate buffered saline. This washing procedure was repeated and then the pellet was re-suspended in phosphate buffered saline to achieve nanocarrier suspension having a nominal concentration of 10 mg/mL on a polymer basis. The suspension was stored frozen at −20° C. until use.

TABLE 1

Nic, R848, OP-II Nanocarrier Characterization

| Nanocarrier ID | Effective Diameter (nm) | TLR Agonist, % w/w | T-cell helper peptide, % w/w |
|---|---|---|---|
| Nic, R848, OP-II | 234 | R848, 0.7 | Ova 323-339, 1.8 |

Materials for Nic,Ø,OP-II Nanocarrier Formulations

Ovalbumin peptide 323-339 amide TFA salt, was purchased from Bachem Americas Inc. (3132 Kashiwa Street, Torrance Calif. 90505. Part #4064565.) PLA with an inherent viscosity of 0.19 dL/g was purchased from Boehringer Ingelheim (Ingelheim Germany. Product Code R202H). PLA-PEG-Nicotine with a nicotine-terminated PEG block of approximately 3,500 Da and DL-PLA block of approximately 15,000 Da was synthesized. Polyvinyl alcohol (MW=11,000-31,000, 87-89% hydrolyzed) was purchased from J.T. Baker (Part Number U232-08).

Methods for Nic,Ø,OP-II Nanocarrier Production

Solutions were prepared as follows:

Solution 1: Ovalbumin peptide 323-339 @69 mg/mL was prepared in 0.13N hydrochloric acid at room temperature.

Solution 2: PLA @75 mg/mL and PLA-PEG-Nicotine @25 mg/mL in dichloromethane was prepared by dissolving PLA @100 mg/mL in dichloromethane and PLA-PEG-Nicotine at 100 mg/mL in dichloromethane, then combining 3 parts of the PLA solution to 1 part of the PLA-PEG-Nicotine solution.

Solution 3: Polyvinyl alcohol @50 mg/mL in 100 mM in deionized water.

Solution 4: 70 mM phosphate buffer, pH 8.

A primary (W1/O) emulsion was first created using Solution 1 and Solution 2. Solution 1 (0.1 mL) and Solution 2 (1.0 mL) were combined in a small glass pressure tube and sonicated at 50% amplitude for 40 seconds using a Branson Digital Sonifier 250. A secondary (W1/O/W2) emulsion was then formed by adding Solution 3 (2.0 mL) to the primary emulsion and sonicating at 35% amplitude for 40 seconds using the Branson Digital Sonifier 250. The secondary emulsion was added to a beaker containing 70 mM phosphate buffer solution (30 mL) in an open 50 ml beaker and stirred at room temperature for 2 hours to allow for the dichloromethane to evaporate and for the nanocarriers to form in suspension. A portion of the suspended nanocarriers were washed by transferring the nanocarrier suspension to centrifuge tubes, spinning at 5300 rcf for 60 minutes, removing the supernatant, and re-suspending the pellet in phosphate buffered saline. This washing procedure was repeated and then the pellet was re-suspended in phosphate buffered saline to achieve nanocarrier suspension having a nominal concentration of 10 mg/mL on a polymer basis. The suspension was stored frozen at −20° C. until use.

TABLE 2

Nanocarrier Characterization

| Nanocarrier ID | Effective Diameter (nm) | TLR Agonist, % w/w | T-cell helper peptide, % w/w |
|---|---|---|---|
| Nic, Ø, OP-II (Ø = no adjuvant) | 248 | None | Ova, 2.2 |

Results

Anti-nicotine antibody titers in mice immunized with NC containing surface nicotine and T-helper peptide OP-II with or without R848 (5 animals/group; s.c., 100 µg of NC per injection, 3 times with 4-wk intervals). Titers for days 26 and 40 after the 1$^{st}$ immunization are shown (ELISA against polylysine-nicotine). Group 1: immunized with NP[Nic, R848,OP-II] (3.1% of NC-conjugated R848); group 2: immunized with NP[Nic,Ø,OP-II] (no R848 bound to NC) admixed with 20 µg of free R848.

Figure 6:
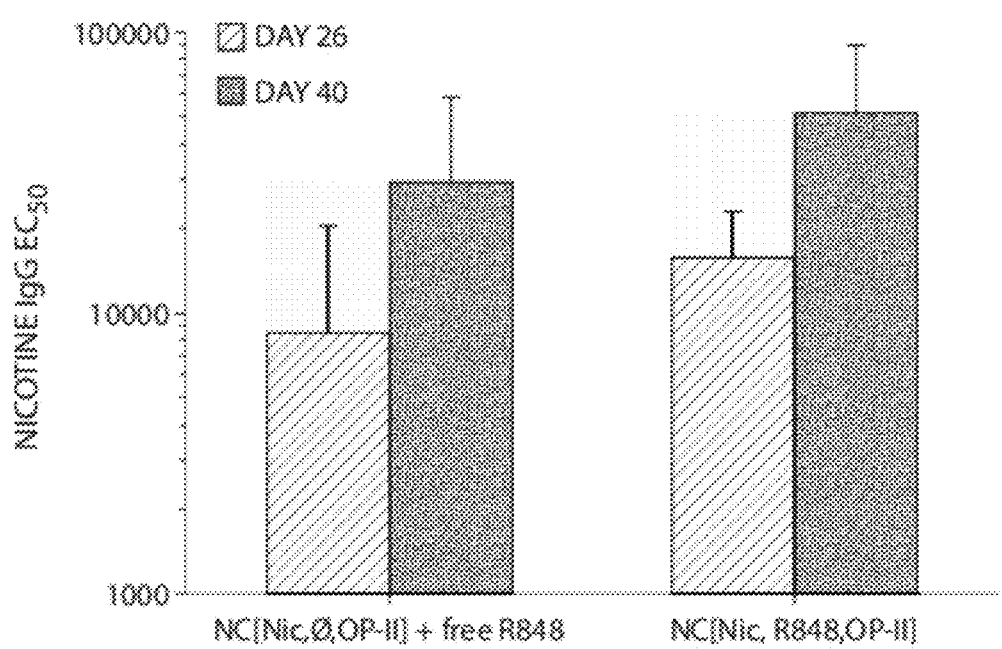
FIG. 6 shows anti-nicotine antibody titers in mice immunized with NC containing surface nicotine and T-helper peptide OP-II with or without R848.
Figure 7A:
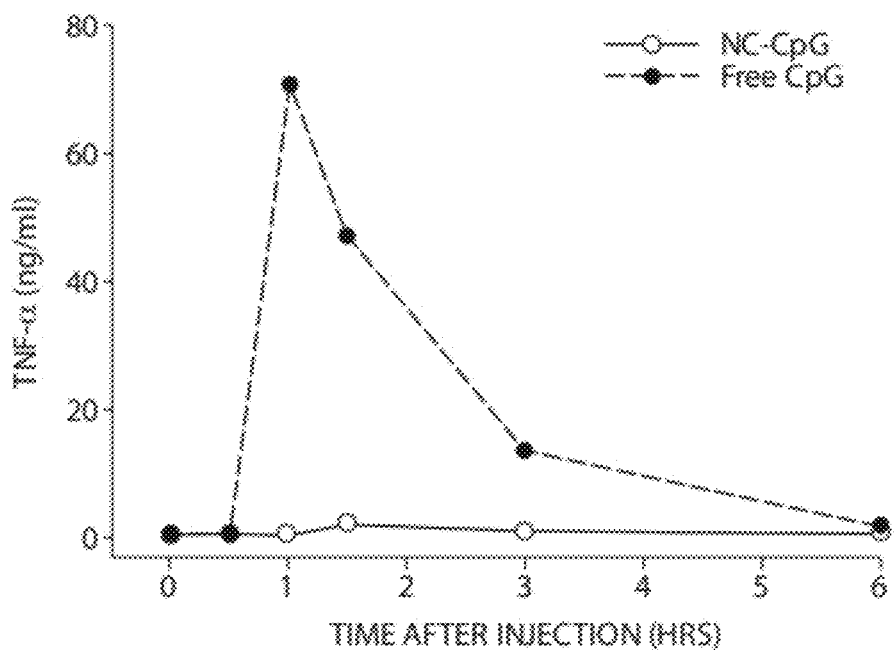
FIG. 7 shows that TNF-α and IL-6 were induced in sera of NC-CpG- and free CpG-inoculated animals.
Figure 7B:
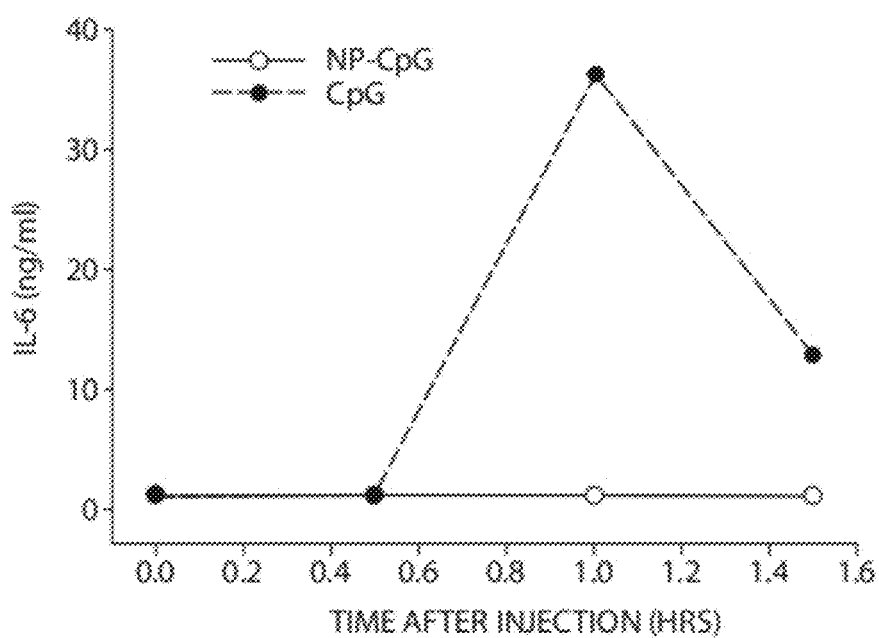
Figure 8:
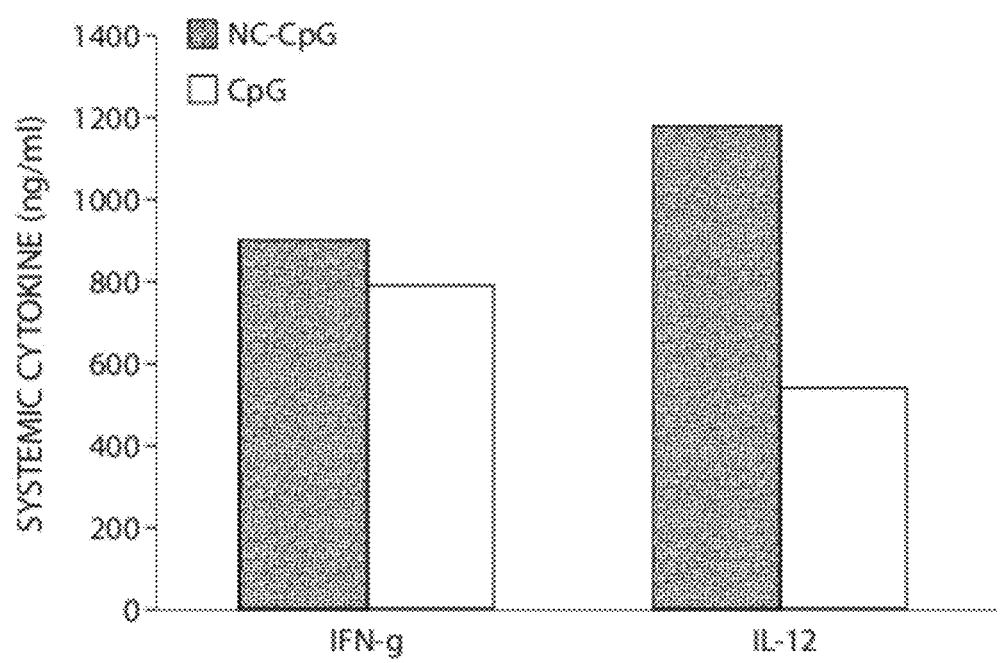
FIG. 8 shows the induction of IFN-γ and IL-12 in sera of NC-CpG- and free CpG-inoculated animals.

These results demonstrate that conjugation of R848 to NC resulted in a stronger adjuvant effect than utilization of free R848 admixed to NC that does not contain R848. When identical amounts of two NCs, one containing surface nicotine, T-helper peptide OP-II and R848 (NC[Nic,R848,OP-II]), and another containing the same ingredients, but without R848 (NC[Nic,Ø,OP-II]) were used for animal immunization, a higher antibody response was observed for R848 that had been conjugated to NC even if a substantially higher amount of free R848 (>6-fold) was admixed to NP[Nic,Ø, OP-II] prior to immunization compared to amount of NC-conjugated R848 (FIG. 6).

Example 12

Nanocarriers with Entrapped Adjuvant Results in Lower Systemic Proinflammatory Cytokine Induction Materials for Nanocarrier Formulations Ovalbumin peptide 323-339 amide acetate salt, was purchased from Bachem Americas Inc. (3132 Kashiwa Street, Torrance Calif. 90505. Product code 4065609.) PS-1826 DNA oligonucleotide with fully phosphorothioated backbone having nucleotide sequence 5'-TCC ATG ACG TTC CTG ACG TT-3' (SEQ ID NO: 2) with a sodium counter-ion was purchased from Oligos Etc (9775 SW Commerce Circle C-6, Wilsonville, Oreg. 97070.) PLA with an inherent viscosity of 0.19 dL/g was purchased from Boehringer Ingelheim (Ingelheim Germany. Product Code R202H). PLA-PEG-Nicotine with a nicotine-terminated PEG block of approximately 5,000 Da and DL-PLA block of approximately 17,000 Da was synthesized. Polyvinyl alcohol (Mw=11,000-31,000, 87-89% hydrolyzed) was purchased from J.T. Baker (Part Number U232-08).

Methods for Nanocarrier Production

Solutions were prepared as follows:

Solution 1: Ovalbumin peptide 323-339 @70 mg/mL in dilute hydrochloric acid aqueous solution. The solution was prepared by dissolving ovalbumin peptide in 0.13N hydrochloric acid solution at room temperature.

Solution 2: 0.19-IV PLA @75 mg/mL and PLA-PEG-nicotine @25 mg/ml in dichloromethane. The solution was prepared by separately dissolving PLA @100 mg/mL in dichloromethane and PLA-PEG-nicotine @100 mg/mL in dichloromethane, then mixing the solutions by adding 3 parts PLA solution for each part of PLA-PEG-nicotine solution.

Solution 3: Oligonucleotide (PS-1826) @200 mg/ml in purified water. The solution was prepared by dissolving oligonucleotide in purified water at room temperature.

Solution 4: Same as solution 2.

Solution 5: Polyvinyl alcohol @50 mg/mL in 100 mM pH 8 phosphate buffer.

Two separate primary water in oil emulsions were prepared. W1/O2 was prepared by combining solution 1 (0.1 mL) and solution 2 (1.0 mL) in a small pressure tube and sonicating at 50% amplitude for 40 seconds using a Branson Digital Sonifier 250. W3/O4 was prepared by combining solution 3 (0.1 mL) and solution 4 (1.0 mL) in a small pressure tube and sonicating at 50% amplitude for 40 seconds using a Branson Digital Sonifier 250. A third emulsion with two inner emulsion phases ([W1/O2,W3/O4]/W5) emulsion was prepared by combining 0.5 ml of each primary emulsion (W1/O2 and W3/O4) and solution 5 (3.0 mL) and sonicating at 30% amplitude for 60 seconds using the Branson Digital Sonifier 250.

The third emulsion was added to an open 50 mL beaker containing 70 mM pH 8 phosphate buffer solution (30 mL) and stirred at room temperature for 2 hours to evaporate dichloromethane and to form nanocarriers in aqueous suspension. A portion of the nanocarriers was washed by transferring the suspension to a centrifuge tube and spinning at 13,800 g for one hour, removing the supernatant, and re-suspending the pellet in phosphate buffered saline. The washing procedure was repeated and the pellet was re-suspended in phosphate buffered saline for a final nanocarrier dispersion of about 10 mg/mL.

The amounts of oligonucleotide and peptide in the nanocarrier were determined by HPLC analysis. The total dry-nanocarrier mass per mL of suspension was determined by a gravimetric method and was adjusted to 5 mg/mL. Particles were stored as refrigerated suspensions until use.

TABLE 3

Nanocarrier Characterization

| | Effective Diameter (nm) | TLR Agonist, % w/w | T-cell helper peptide, % w/w |
|---|---|---|---|
| Nanocarrier | 232 | PS-1826, 6.4 | Ova, 2.2 |

Results

TNF-α and IL-6 were induced in sera of NC-CpG- and free CpG-inoculated animals. Animal groups were inoculated (s.c.) either with 100 µg of NC-CpG (containing 5% CpG-1826) or with 5 µg of free CpG-1826. At different time-points post inoculation serum was collected from the animals (3/group) by terminal bleed, pooled and assayed for cytokine presence in ELISA (BD).

The results demonstrate that entrapment of adjuvant within NC results in a lower immediate systemic proinflammatory cytokine induction than utilization of free adjuvant. When identical amounts of a CpG adjuvant, NC-entrapped or free, were used for inoculation, a substantially higher induction of TNF-α and IL-6 in animal serum was observed for free CpG compared to NC-entrapped CpG (FIG. 7).

Example 13

Nanocarriers with Entrapped Adjuvant Results in Similar or Higher Long-Term Systemic Induction of Immune Cytokines Materials for Nanocarrier Formulations Ovalbumin peptide 323-339 amide acetate salt, was purchased from Bachem Americas Inc. (3132 Kashiwa Street, Torrance Calif. 90505. Product code 4065609.) PS-1826 DNA oligonucleotide with fully phosphorothioated backbone having nucleotide sequence 5'-TCC ATG ACG TTC CTG ACG TT-3' (SEQ ID NO: 2) with a sodium counter-ion was purchased from Oligos Etc (9775 SW Commerce Circle C-6, Wilsonville, Oreg. 97070.) PLA with an inherent viscosity of 0.21 dL/g was purchased from SurModics Pharmaceuticals (756 Tom Martin Drive, Birmingham, Ala. 35211. Product Code 100 DL 2A.) PLA-PEG-Nicotine with a nicotine-terminated PEG block of approximately 5,000 Da and DL-PLA block of approximately 17,000 Da was synthesized. Polyvinyl alcohol (MW=11,000-31,000, 87-89% hydrolyzed) was purchased from J.T. Baker (Part Number U232-08).

Methods for Nanocarrier Production

Solutions were prepared as follows:

Solution 1: Ovalbumin peptide 323-339 @35 mg/mL in dilute hydrochloric acid aqueous solution. The solution was prepared by dissolving ovalbumin peptide in 0.13N hydrochloric acid solution at room temperature.

Solution 2: 0.21-IV PLA @75 mg/mL and PLA-PEG-nicotine @25 mg/ml in dichloromethane. The solution was prepared by separately dissolving PLA @100 mg/mL in dichloromethane and PLA-PEG-nicotine @100 mg/mL in dichloromethane, then mixing the solutions by adding 3 parts PLA solution for each part of PLA-PEG-nicotine solution.

Solution 3: Oligonucleotide (PS-1826) @200 mg/ml in purified water. The solution was prepared by dissolving oligonucleotide in purified water at room temperature.

Solution 4: Same as Solution #2.

Solution 5: Polyvinyl alcohol @50 mg/mL in 100 mM pH 8 phosphate buffer.

Two separate primary water in oil emulsions were prepared. W1/O2 was prepared by combining solution 1 (0.2 mL) and solution 2 (1.0 mL) in a small pressure tube and sonicating at 50% amplitude for 40 seconds using a Branson Digital Sonifier 250. W3/O4 was prepared by combining solution 3 (0.1 mL) and solution 4 (1.0 mL) in a small pressure tube and sonicating at 50% amplitude for 40 seconds using a Branson Digital Sonifier 250. A third emulsion with two inner emulsion ([W1/O2,W3/O4]/W5) emulsion was prepared by combining 0.55 ml of each primary emulsion (W1/O2 and W3/O4) and solution 5 (3.0 mL) and sonicating at 30% amplitude for 60 seconds using the Branson Digital Sonifier 250.

The third emulsion was added to an open 50 mL beaker containing 70 mM pH 8 phosphate buffer solution (30 mL) and stirred at room temperature for 2 hours to evaporate dichloromethane and to form nanocarriers in aqueous suspension. A portion of the nanocarriers was washed by transferring the suspension to a centrifuge tube and spinning at 13,800 g for one hour, removing the supernatant, and re-suspending the pellet in phosphate buffered saline. The washing procedure was repeated and the pellet was re-suspended in phosphate buffered saline for a final nanocarrier dispersion of about 10 mg/mL.

The amounts of oligonucleotide and peptide in the nanocarrier were determined by HPLC analysis. The total dry-nanocarrier mass per mL of suspension was determined by a gravimetric method and was adjusted to 5 mg/mL. Particles were stored as refrigerated suspensions until use.

TABLE 4

Nanocarrier Characterization

| | Effective Diameter (nm) | TLR Agonist, % w/w | T-cell helper peptide, % w/w |
|---|---|---|---|
| Nanocarrier | 217 | PS-1826, 6.2 | Ova, Not Determined |

Results

IFN-γ and IL-12 were induced in sera of NC-CpG- and free CpG-inoculated animals. Animal groups were inoculated (s.c.) with 100 μg of NC-CpG (containing 6% CpG-1826) or with 6 μg of free CpG-1826. At 24 hours post inoculation serum was collected from the animals (3/group) by terminal bleed, pooled and assayed for cytokine presence in ELISA (BD).

These results demonstrate that entrapment of adjuvant within nanocarriers results in a similar or even higher long-term systemic induction of immune cytokines compared to utilization of free adjuvant. When identical amounts of a CpG adjuvant, NC-entrapped or free, were used for animal inoculation, a similar level of long-term induction of systemic IFN-γ and higher induction of IL-12 in animal serum was observed (FIG. 8).

What is claimed is:

1. A method for increasing local immune cytokine induction but not systemic induction of pro-inflammatory cytokines comprising:
   generating a systemic cytokine release through administration to a subject of a dose of an adjuvant, wherein at least a portion of the dose of the adjuvant is coupled to synthetic nanocarriers and
   choosing the dose of the coupled adjuvant to be greater than a separate dose of the adjuvant which is not coupled to synthetic nanocarriers, wherein the administration of the coupled adjuvant results in a systemic cytokine release similar to that generated through administration of the dose of the not-coupled adjuvant to the subject.

2. The method of claim 1, wherein the method further comprises providing the dose of adjuvant.

3. The method of claim 1 or 2, wherein the adjuvant comprises an agonist for Toll-Like Receptors 3, 4, 5, 7, 8, or 9 or a combination thereof.

4. The method of claim 1 or 2, wherein the dose of adjuvant comprises two or more types of adjuvants.

5. The method of claim 1 or 2, wherein the method further comprises administering more than one type of antigen to the subject.

6. The method of claim 5, wherein at least a portion of the dose of antigen(s) is coupled to the synthetic nanocarriers.

7. The method of claim 5, wherein the antigen(s) comprise a B cell antigen or a T cell antigen or both.

8. The method of claim 1 or 2, wherein the synthetic nanocarriers comprise lipid nanoparticles, polymeric nanoparticles, metallic nanoparticles, surfactant-based emulsions, dendrimers, buckyballs, nanowires, virus-like particles, peptide or protein particles, nanoparticles that comprise a combination of nanomaterials, spheroidal nanoparticles, cuboidal nanoparticles, pyramidal nanoparticles, oblong nanoparticles, cylindrical nanoparticles, or toroidal nanoparticles.

9. The method of claim 1 or 2, wherein the synthetic nanocarriers comprise one or more polymers.

10. The method of claim 1 or 2, wherein at least one dosage form comprises the dose of adjuvant.

11. The method of claim 1 or 2, wherein the subject has cancer, an infectious disease, a non-autoimmune metabolic disease, a degenerative disease, an addiction, and atopic condition, asthma, chronic obstructive pulmonary disease (COPD) or a chronic infection.

* * * * *